United States Patent
Dugar et al.

(10) Patent No.: US 9,556,140 B2
(45) Date of Patent: Jan. 31, 2017

(54) APPROACH FOR SYNTHESIS OF CATECHINS

(71) Applicant: Sphaera Pharma Pvt. Ltd., IMT Manesar (IN)

(72) Inventors: Sundeep Dugar, IMT Manesar (IN); Dinesh Mahajan, IMT Manesar (IN); Kumar Santosh Rai, IMT Manesar (IN); Vinayak Tripathi, IMT Manesar (IN); Ishwar Rakesh Patil, IMT Manesar (IN)

(73) Assignee: Sphaera Pharma Pvt. Ltd., Haryana (IN)

( * ) Notice: Subject to any disclaimer, the term of this patent is extended or adjusted under 35 U.S.C. 154(b) by 0 days.

(21) Appl. No.: 14/763,018

(22) PCT Filed: Jan. 27, 2014

(86) PCT No.: PCT/IN2014/000061
§ 371 (c)(1),
(2) Date: Jul. 23, 2015

(87) PCT Pub. No.: WO2014/115174
PCT Pub. Date: Jul. 31, 2014

(65) Prior Publication Data
US 2015/0368223 A1  Dec. 24, 2015

(30) Foreign Application Priority Data

Jan. 26, 2013 (IN) .......................... 2315/DEL/2012

(51) Int. Cl.
| | | |
|---|---|---|
| *C07D 311/62* | (2006.01) | |
| *A61K 31/353* | (2006.01) | |
| *C07D 311/30* | (2006.01) | |
| *C07D 311/32* | (2006.01) | |
| *C07F 7/18* | (2006.01) | |

(52) U.S. Cl.
CPC ........... *C07D 311/62* (2013.01); *A61K 31/353* (2013.01); *C07D 311/30* (2013.01); *C07D 311/32* (2013.01); *C07F 7/1856* (2013.01)

(58) Field of Classification Search
CPC ............................ C07D 311/62; A61K 31/353
See application file for complete search history.

(56) References Cited

U.S. PATENT DOCUMENTS 6,365,757 B1 *  4/2002  Chattopadhyay .... C07D 311/60
                                                         549/403
9,375,684 B2 *  6/2016  Bhattacharyya ... B01D 67/0079

FOREIGN PATENT DOCUMENTS

| WO | WO-02/20506 | 3/2002 |
| WO | WO-2007/002877 A1 | 1/2007 |
| WO | WO-2012/101652 A2 | 8/2012 |

OTHER PUBLICATIONS

International Search Report dated Dec. 24, 2014, from PCT/IN2014/000061.
J.P.J. Marais et al., The Science of Flavonoids, Chapter 1. The Sterochemistry of Flavonoids, 2006, Springer Science and Business Media Inc., pp. 1-46.

* cited by examiner

*Primary Examiner* — Golam M M Shameem
(74) *Attorney, Agent, or Firm* — Foley Hoag LLP

(57) ABSTRACT

A process for synthesis of enatiomerically pure or enatiomerically enriched or racemic mixture of (+ and/or −) epicatechin and its intermediates, comprising the steps of: (i) obtaining penta-protected quercetin; (ii) reducing the penta-protected quercetin obtained from step (i); (iii) optionally deprotecting the compound of step (ii); (iv) reducing the compound obtained from step (ii) or step (iii) in the presence of a chiral/achiral reducing agent to obtain a chiral intermediate; (v) deprotecting and/or hydrogenation of the chiral intermediate obtained from step (iv) to obtain (−)-epicatechin; (vi) optionally simultaneously deprotecting and by drogenation of the compound obtained from step (ii) to obtain racemic epicatechin.

9 Claims, No Drawings

APPROACH FOR SYNTHESIS OF CATECHINS

RELATED APPLICATIONS

Figure 1:
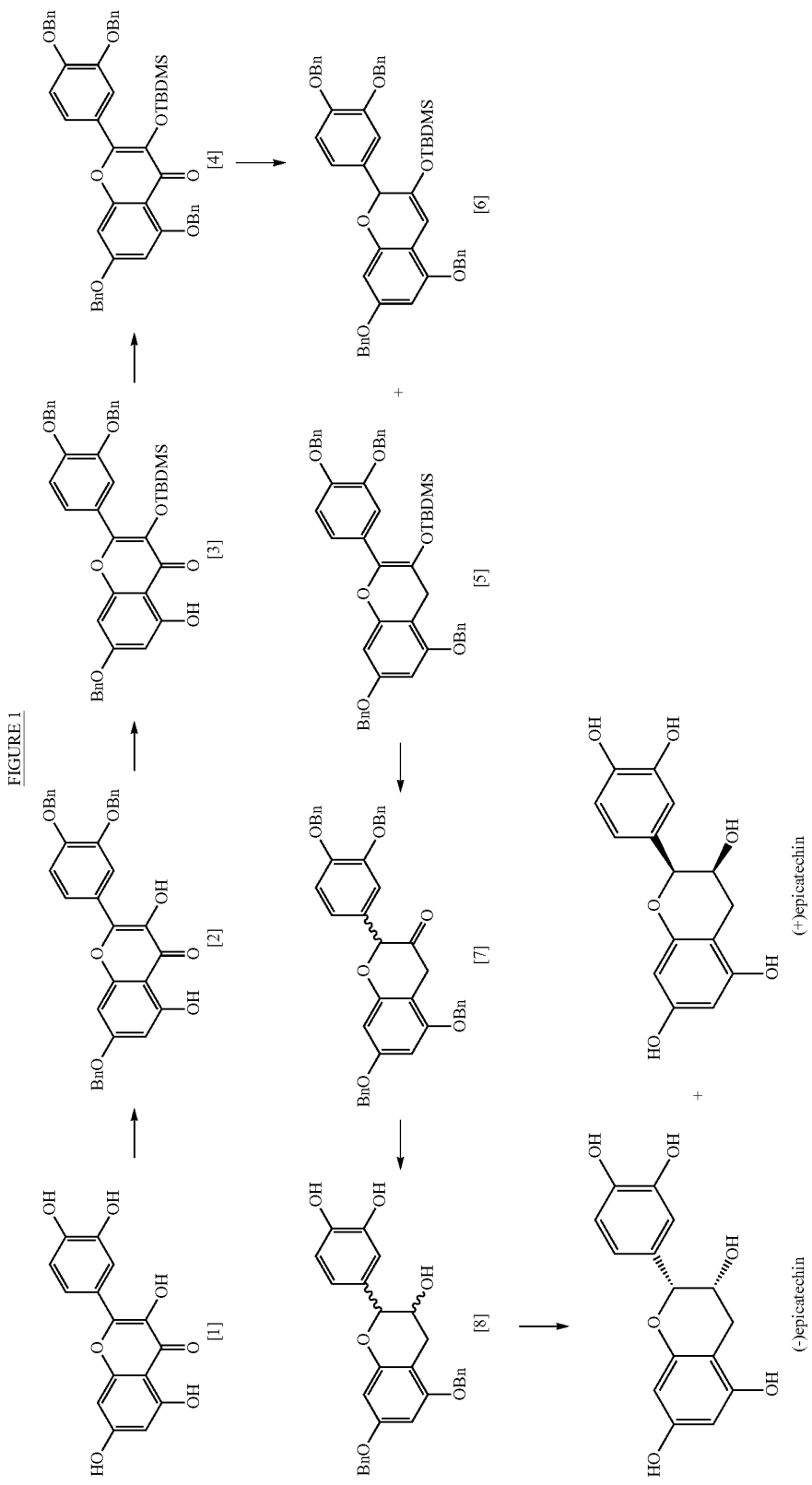

This application is the National Stage application of PCT/IN2014/000061, filed Jan. 27, 2014, which claims priority to Indian provisional patent application 2315/DEL/2012, filed Jan. 26, 2013; each application is hereby incorporated in its entirety by this reference.

FIELD OF THE INVENTION

The present invention provides a process for synthesis of enatiomerically pure or enatiomerically enriched or racemic mixture of (+ and/or −) epicatechin and its intermediates such as 2H chromene, 4H chromene, cyanidin either as racemates or as their enantiomerically enriched form.

BACKGROUND OF THE INVENTION

Polyphenolic natural products are of current interest because of their numerous biological activities, and their resulting relevance for human health. Polyphenolic natural products have more than one and often several hydroxyl groups. Several different hydroxylation patterns have been found in nature. Representative examples include: (−)-epi-afzelechin, (+)-catechin, (−)-epicatechin, (−)-gallocatechin, (−)-epigallocatechin, their respective 3-gallate esters, as well as two 3-(30-methyl) gallate esters, which are referred to collectively herein as "catechins". (+)-Catechin, (−)-catechins, (+)-epicatechin and (−)-epicatechin are flavan-3-ols. Catechins are present in the human diet in chocolate, fruits, vegetables and wine, have found use in the treatment of acute coronary syndromes, including but not limited to myocardial infarction and angina; acute ischemic events in other organs and tissues, including but not limited to renal injury, renal ischemia and diseases of the aorta and its branches; injuries arising from medical interventions, including but not limited to coronary artery bypass grafting (CABG) procedures and aneurysm repair; cancer; and metabolic diseases, including but not limited to diabetes mellitus. Health benefits of catechins have been broadly attributed to their antioxidant and mitochondria biogenesis properties, effects on intestinal microorganisms and nutrient absorption, and effects on metabolism and metabolic enzymes.

Catechins for use as pharmaceutical and nutraceutical preparations have been obtained through plant extraction, followed if desired by purification of individual catechin species using chromatographic methods. However, often the availability of various purified catechins from natural sources is very limited and expensive. Also the current processes, particularly for the synthesis of epicatechin of desired stereochemistry, either involve very expensive starting materials and/or reagents, or are synthetically challenging and not amenable for larger scale synthesis.

Certain processes for synthesis of epicatechin are available in prior art. One such process is disclosed in PCT/IN2012/000052. The present invention involves novel intermediates and is amenable to commercial scale-up. Hence, it is an objective to provide an efficient and cost effective synthetic method for the synthesis of cis-catechin/epicatechin and its intermediates in their enatiomerically pure or enatiomerically enriched forms.

OBJECT OF THE INVENTION

An object of the invention is to provide a novel method of synthesis of epicatechin in enatiomerically pure or isomerically enriched and/or racemic forms.

Another object of the invention is to provide intermediates of epicatechin in enatiomerically pure or isomerically enriched and/or racemic forms.

SUMMARY OF THE INVENTION

The present invention provides a novel process for synthesis of enatiomerically pure or enatiomerically enriched or racemic mixture of (+ and/or −) epicatechin and its intermediates, comprising the steps of:
I. obtaining penta-protected quercetin;
II. reducing the penta-protected quercetin obtained from step (i);
III. optionally deprotecting the compound of step (ii);
IV. reducing the compound obtained from step (ii) or step (iii) in the presence of a chiral/achiral reducing agent to obtain a chiral intermediate;
V. deprotecting and/or hydrogenation of the chiral intermediate obtained from step (iv) to obtain (−)-epicatechin.
VI. Optionally simultaneously deprotecting and hydrogenation of the compound obtained from step (ii) to obtain racemic epicatechin.

DETAILED DESCRIPTION OF THE INVENTION

The present invention relates to synthesis of epicatechin and other related polyphenols, natural or designed, or various intermediates in the synthesis of epicatechin and other related polyphenols, natural or designed, such as 2H chromene, 4H chromene, cyanidin etc.

The various compounds and other intermediates may be synthesized by varying the starting material and the chemical reaction. For instance, the various intermediates may be obtained as depicted in the scheme A below:

Scheme A

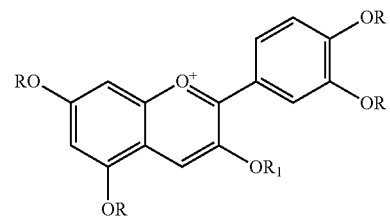

4A

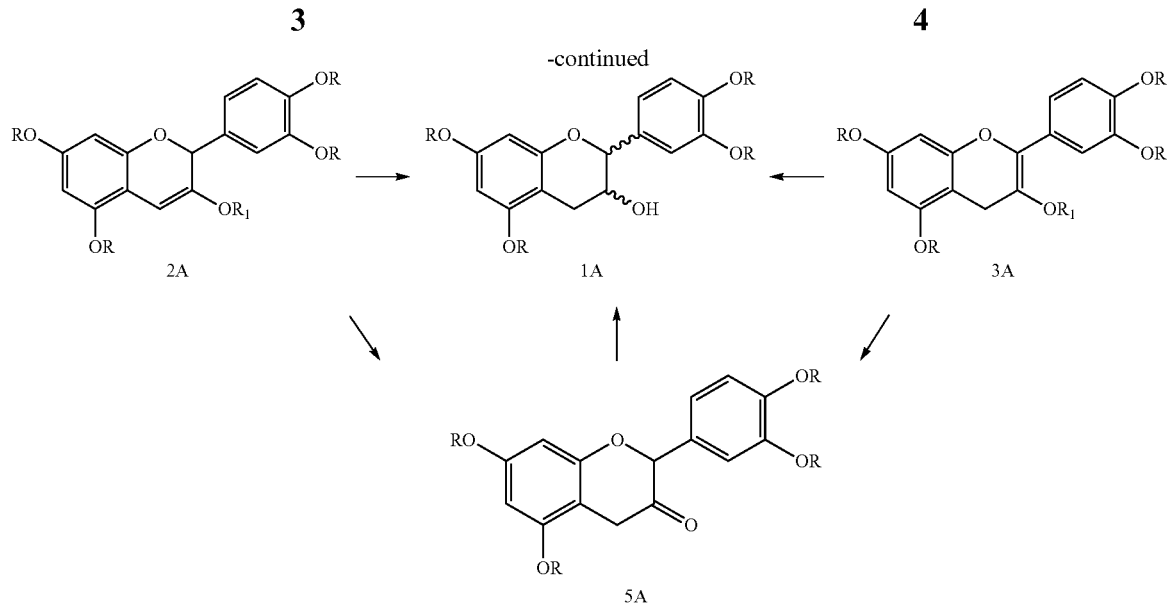

Wherein R and R1 may be any protecting group selected from the group consisting of H, Ac, Bn, Allyl, propargyl, benzyl, 2-fluoroethyl, 4-nitrobenzyl, 4-chlorobenzyl, 4-methoxybenzyl, 4-methoxybenzonitrile, cinnamyl, methyl 4-crotonyl, but-2-en-1-yl, 2-pentenyl, (3-prop-len-lyl)sulfonyl benzene, 1-trimethylsilyl-prop-1-yn-3-yl, 2-octyne-1-yl, 2-butyne-1-yl, 2-picolyl, 3-picolyl, 4-picolyl, quinolin-4-yl-methyl, acetonitrile, 2-methyl-oxirane, fluoromethyl, nitromethyl, methyl acetate-2-yl, methoxymethyl, acetamide, 1-phenylethanone-2-yl, 2-butanone-1-yl, chloromethyl, methyl phenyl sulfone, 1-bromo-prop-1-ene-3-yl, t-butyl, methyl, ethyl, allyl, t-butyldimethylsilyl, trimethylsilyl and t-butyldiphenylsilylethyl.

In order to obtain the various compounds as depicted in scheme A, the synthetic schemes 1, 2 or 3 as represented in the present invention may be employed.

Accordingly, the present invention provides a process for synthesis of enatiomerically pure or enatiomerically enriched or racemic mixture of (+ and/or −) epicatechin and its intermediates, comprising the steps of:

I. obtaining penta-protected quercetin;
II. reducing the penta-protected quercetin obtained from step (i);
III. optionally deprotecting the compound of step (ii);
IV. reducing the compound obtained from step (ii) or step (iii) in the presence of a chiral/achiral reducing agent to obtain a chiral intermediate;
V. deprotecting and/or hydrogenation of the chiral intermediate obtained from step (iv) to obtain (−)-epicatechin.
VI. Optionally simultaneously deprotecting and hydrogenation of the compound obtained from step (ii) to obtain racemic epicatechin.

The present invention uses a suitable starting material, wherein starting material may be obtained from natural or synthetic sources. Preferably the starting material is quercetin or catechin. More preferably the starting material is quercetin.

The penta-protected quercetin of step (I) is obtained in one or more than one selective protection steps. The selective protection of the hydroxyl groups of quercetin is carried out in the presence of a protecting agent, a base and a polar organic solvent at atmospheric pressure, at a temperature in the range of 0-80° C. The protecting agent is selected from the group consisting of allyl bromide, propargyl bromide, benzyl bromide, benzyl chloride, 2-fluoroethyl bromide, 4-nitrobenzyl bromide, 4-chlorobenzyl bromide, 4-methoxybenzyl bromide, α-bromo-p-tolunitrile, cinnamyl bromide, methyl 4-bromocrotonate, crotyl bromide, 1-bromo-2-pentene, 3-bromo-1-propenyl phenyl sulfone, 3-bromo-1-trimethylsilyl-1-propyne, 3-bromo-2-octyne, 1-bromo-2-butyne, 2-picolyl chloride, 3-picolyl chloride, 4-picolyl chloride, 4-bromomethyl quinoline, bromoacetonitrile, epichlorohydrin, bromofluoromethane, bromonitromethane, methyl bromoacetate, methoxymethyl chloride, bromoacetamide, 2-bromoacetophenone, 1-bromo-2-butanone, bromo chloromethane, bromomethyl phenyl sulfone, 1,3-dibromo-1-propene, trimethyl silyl chloride and tert-Butyldimethylsilyl chloride. The base is selected from the group consisting of alkali metal hydride such as sodium hydride, dialkylamide, bis(trialkylsilyl)amide, diazabicycloundecene (DBU), alkali metal carbonates such as potassium carbonate ($K_2CO_3$) or alkali metal hydroxide and the polar organic solvent is selected from the group consisting of acetone, acetonitrile, tetrahydrofuran (THF), ethyl acetate, dioxane, N,N-dimethylformamide (DMF), dichloromethane (DCM), a sulfoxide such as dimethylsulfoxide (DMSO), or N-methylpyrrolidinone (NMP), preferably the solvent is NMP and a mixture of NMP and acetone.

The reduction of step (II) is carried out in the presence of a reducing agent selected from the group consisting of sodium amalgam, zinc mercury amalgam; metal, hydrides including sodium hydride (NaH), Lithium Aluminum hydride (LAH); vitride solution [$NaAlH_2(OCH_2CH_2OCH_3)_2$ in toluene] with or without a Lewis acid selected from the group consisting of aluminum chloride, cerium chloride, zinc chloride, boron triflouride, and iodine.

The chiral/achiral reducing agent of step (IV) is selected from the group consisting of sodium borohydride ($NaBH_4$), $NaCNBH_3$ (sodium cyanoborohydride), potassium borohydride ($KBH_4$), lithium borohydride ($LiBH_4$), 9-Borabicyclo[3.3.1]nonane(9-BBN), 'S' or 'R.' alpine borane or (−) diisopinocampheylborane, L-selectride (lithium tri-sec-butyl(hydrido)borate(1−)), Willkinsons catayst, 2,3-dichloro-5,6-dicyano-1,4-benzoquinone, Hantzsch Ester, aluminum hydride, diisobutyl aluminum hydride, trialkoxy aluminum hydride and sodium bis(2-methoxy ethoxy) aluminium hydride.

The deprotection of step (V) is performed using hydrogen gas in the presence of a hydrogenation catalyst adsorbed onto a solid support, and a solvent or a mixture of solvents at a temperature in the range of 20-60° C. The hydrogenation catalyst is selected from the group consisting of platinum, palladium or nickel and the solvent is selected from the group consisting of methanol, ethanol, ethyl acetate, tetrahydrofuran, acetic acid or mixtures thereof, preferably the hydrogenation catalyst is palladium on carbon.

The chemical reactions of protection, deprotection, hydroxylation and reduction of the present invention may be conducted as per the procedures below:

(A) Protection and De-Protection

Suitable methods for protection of groups as disclosed in the present invention include methods for protection of the hydroxyl group. Suitable methods of protection of hydroxyl group include formation of ethers, esters, acetates, chloroacetates, trifuluroacetates, pivaloates, benzoates, 1,2 and 1,3-diols, isopropylidenes, alkylation, silylation, etc. Suitable methods for deprotection will depend upon the protective group employed.

A suitable method of protection of the hydroxyl groups involves alkylation. Alkylating agents include alkyl chlorides, bromides, iodides or alkyl sulfonates. Specific examples of alkylating agents include allyl bromide, propargyl bromide, benzyl bromide, benzyl chloride, 2-fluoroethyl bromide, 4-nitrobenzyl bromide, 4-chlorobenzyl bromide, 4-methoxybenzyl bromide, α-bromo-p-tolunitrile, cinnamyl bromide, methyl 4-bromocrotonate, crotyl bromide, 1-bromo-2-pentene, 3-bromo-1-propenyl phenyl sulfone, 3-bromo-1-trimethylsilyl-1-propyne, 3-bromo-2-octyne, 1-bromo-2-butyne, 2-picolyl chloride, 3-picolyl chloride, 4-picolyl chloride, 4-bromomethyl quinoline, bromoacetonitrile, epichlorohydrin, bromofluoromethane, bromonitromethane, methyl bromoacetate, methoxymethyl chloride, bromoacetamide, 2-bromoacetophenone, 1-bromo-2-butanone, bromo chloromethane, bromomethyl phenyl sulfone and 1,3-dibromo-1-propene. A suitable reagent for alkylation is a benzyl halide, such as benzyl bromide. Silylating agents includes but not limited to tert-Butyldimethylsilyl chloride.

The base may be selected from alkali metal hydride such as NaH, dialkylamide, bis(trialkylsilyl)amide, hydroxide, alkali metal hydroxide, diazabicycloundecene (DBU), carbonates more preferably an alkali metal carbonate such as potassium carbonate.

The solvent may be selected from acetone, acetonitrile, tetrahydrofuran (THF), ethyl acetate, dioxane, N,N-dimethylformamide (DMF), dichloromethane (DCM), a sulfoxide such as dimethylsulfoxide (DMSO), N-methylpyrrolidinone (NMP) or mixture thereof. Preferably the solvent is DMF.

Quercetin or catechin is stirred in a solvent and a base is added at a temperature in the range of 0° C. to reflux under nitrogen atmosphere. To the stirred solution, a protecting agent is added dropwise and the mixture is stirred at a temperature in the range of 0° C. to reflux. After complete consumption of the reactant, the reaction mixture is quenched with water and extracted with suitable solvent. The combined organic layer is washed with water, brine and dried over sodium sulphate. The organic layer is rotary evaporated to afford to obtain crude product which is then loaded on to silica gel column and eluted with suitable eluents to afford protected quercetin/catechin. The protection of hydroxyl groups may be carried out in one or more steps.

Deprotection reaction is carried out in the presence of suitable deprotecting reagents selected from tetrabutyl ammonium bromide, tetrabutyl ammonium fluoride (TBAF) in the presence of solvents selected from the group of THF, DMF, DCM, DMSO, NMP, acetone, ethyl acetate or mixtures thereof at a temperature in the range of –10° C. to 0° C. under nitrogen or hydrogen atmosphere.

(B) Reduction

Reduction reactions of the present invention include the use of suitable chiral/achiral reducing agents such as metal hydride which may include sodium hydride (NaH), Lithium Aluminum hydride (LAH), sodium borohydride (NaBH$_4$), NaCNBH$_3$, potassium borohydride (KBH$_4$), lithium borohydride (LiBH$_4$), 9-Borabicyclo[3.3.1]nonane(9-BBN), Vitride, L-selectride, Willkinsons catayst, Hantzsch Ester, aluminum hydride, diisobutyl aluminum hydride, trialkoxy aluminum hydride with or without Lewis acids such as aluminum chloride, cerium chloride, zinc chloride, boron triflouride, and iodine. Further, a suitable reducing reagent may include sodium amalgam, zinc mercury amalgam.

Preferably the achiral reducing agent is lithium aluminum hydride.

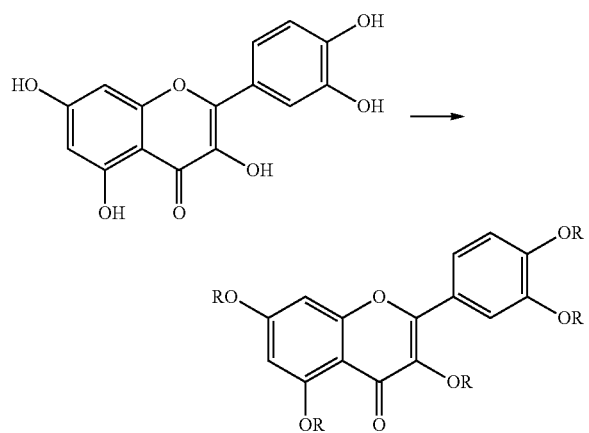

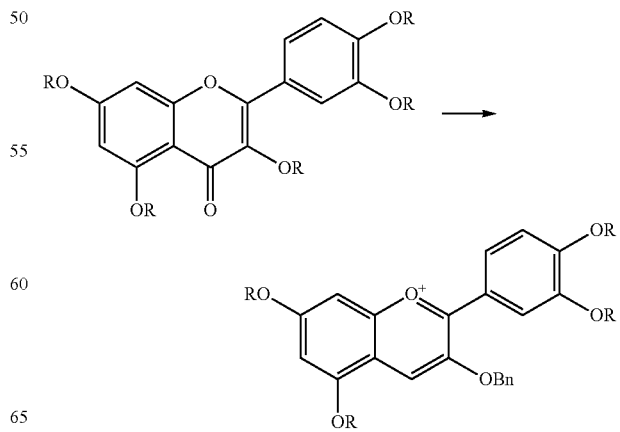

The protection of the hydroxyl group by alkylation reaction is carried out in the presence of a strong base and a polar organic solvent.

The chiral/achiral reducing agents which result in chiral intermediates are selected from the group consisting of sodium borohydride (NaBH$_4$), NaCNBH$_3$ (sodium cyanoborohydride), potassium borohydride (KBH$_4$), lithium borohydride (LiBH$_4$), 9-Borabicyclo[3.3.1]nonane(9-BBN), 'S' or 'R' alpine borane or (−) diisopinocampheylborane, L-selectride (lithium tri-sec-butyl(hydrido)borate(1−)), Willkinsons catayst, 2,3-dichloro-5,6-dicyano-1,4-benzoquinone, Hantzsch Ester, aluminum hydride, diisobutyl aluminum hydride, trialkoxy aluminum hydride and sodium bis(2-methoxy ethoxy) aluminium hydride.

The reduction with suitable chiral/achiral reducing agents afford chiral 2H-chromene or chiral 4H-chromene or 2H-chromene analogs which when subjected to hydrogenation in presence of palladium in hydrogen atmosphere afforded chirally pure product or a racemic mixture.

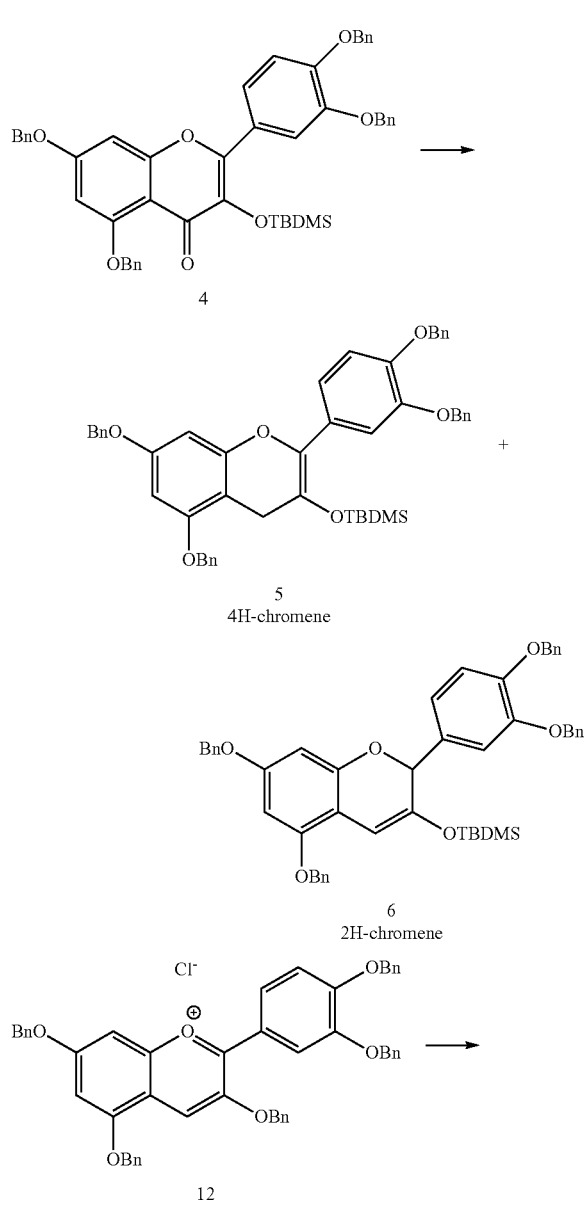

The chiral reducing agent is selected from the group consisting of borane preferably 'S' or 'R' alpine borane or (−) Diisopinocampheylborane.

The reaction may be carried out in a temperature ranging from −78° C. to 70° C. This reaction may preferably be carried out in an atmosphere of hydrogen gas or Nitrogen gas in a suitable organic solvent such as methanol, ethanol, diethyl ether, toluene, ACN, dichloromethane, ethyl acetate, tetrahydrofuran (THF), acetic acid, ethyl acetate, methyl t-butyl ether (MTBE) etc. or mixtures thereof.

Reduction may be carried out in an atmosphere of hydrogen gas in the presence of a solvent with suitable catalyst such as Pd, Pt, Ni etc. adsorbed onto a solid support.

A preferred method is by the use of hydrogen in presence of 10% palladium and carbon.

The reaction is carried out in the presence of solvents selected from methanol, ethanol, ethyl acetate, THF or acetic acid, preferably the solvent is methanol.

The reaction may be carried out at a temperature ranging from 25° C.-60° C. and at a pressure ranging from 4-50 psi.

In an embodiment, reduction may be carried out by use of 10% Pd(OH)$_2$ on activated charcoal.

If protection of the quercetin is by benzyl groups, deprotection may be facilitated by hydrogenolysis.

The compounds may be obtained as a racemic mixture or as pure compounds.

(C) Hydroxylation Reaction

The hydroxylation of the compound may be carried out either by a chemical process or by a biological process. Preferably the hydroxylation is carried out by chemical means. The hydroxylation reaction may be carried out by the use of reagent such as DDQ (2,3-dichloro-5,6-dicyanobenzoquinone) in a suitable solvent systems such as DCM and/or water at temperature ranging from ambient to refluxing.

(D) Elimination Reaction

The Elimination reaction may be through either E1 or E2 mechanism. The Elimination may be just a water molecule. Such reactions may be conducted in presence of reagent such as MsCl and base such as triethylamine in a solvent such as dichloroethane at temperature ranging from ambient to refluxing.

(E) Resolution

The compounds may be obtained as racemic mixture, or enriched in one of the two enantiomers and is resolved into optically pure enantiomers using techniques such as chiral preparative liquid chromatography using an appropriate chiral phase, such as, but not limited to bonded polysaccharide phase, enzyme resolution using enzymes such as, but not limited to, human or pig liver esterases, lipase-catalyzed asymmetric transesterification via use of an appropriate lipase and vinyl ester, or by the partial crystallization of the diastereomers generated by the functionalization of one of the hydroxyl groups of epicatechin with acids or anhydrides such as mandelic acid, tartaric acid derivatives such as di-p-toluoyltartaric anhydride etc, followed by separation of a highly enriched single enantiomer as the ester and highly enriched other enantiomer as the unreacted alcohol.

In one aspect, the +/− epicatechins/intermediates of the present invention may be obtained by subjecting quercetin using reactions as represented in Synthetic Schemes 1and 2.

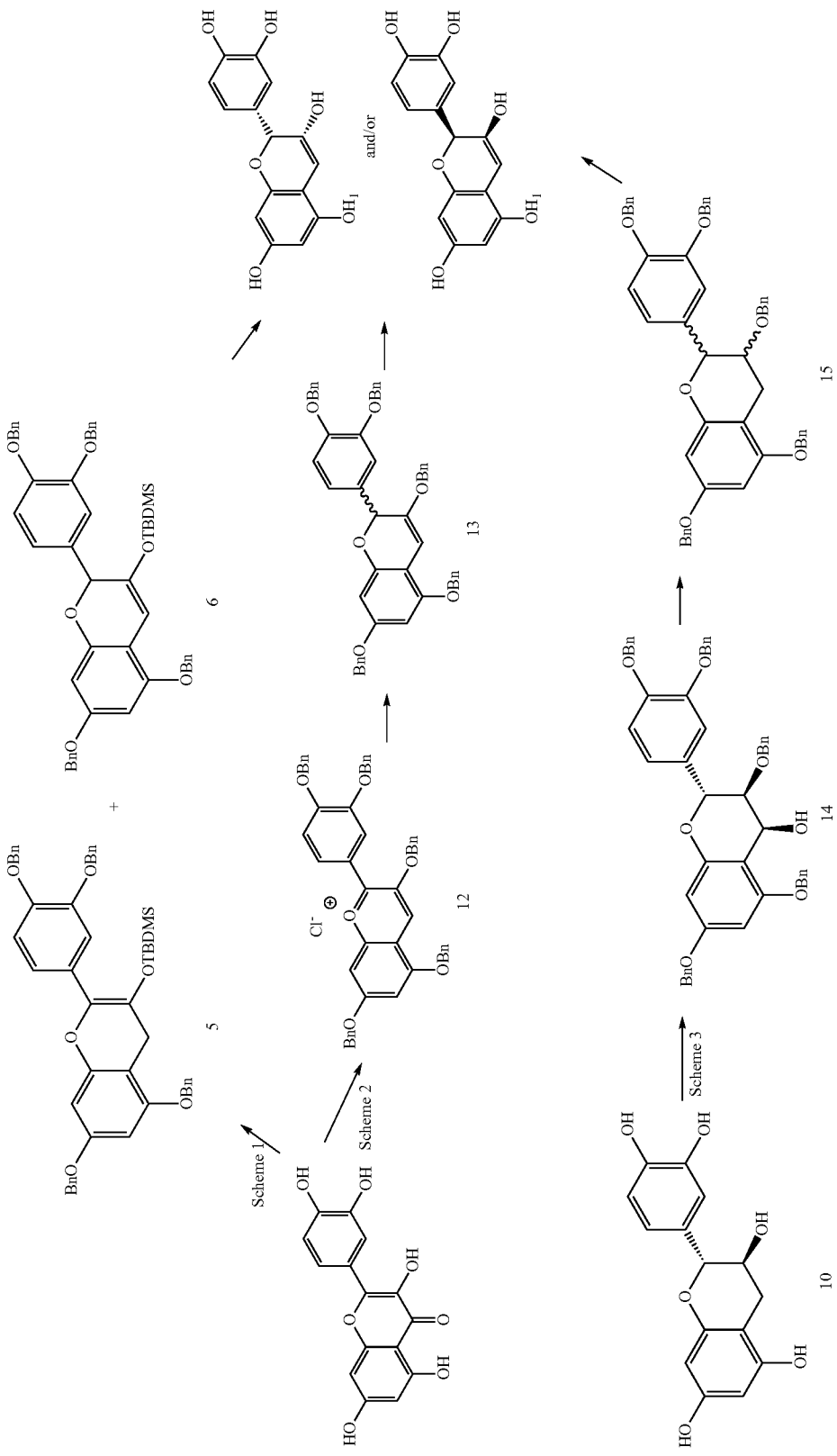

In another embodiments, the +/− epicatechins/intermediates of the present invention may also be obtained by subjecting catechin using reactions as represented in Synthetic Scheme 3.

Synthetic Scheme 1:

As illustrated in Figure 1, the (±) epicatechin is obtained by a process comprising the steps of:
i. selective protection of hydroxyl groups of Quercetin at 7, 3' and 4' positions;
ii. further protection of hydroxyl group of compound obtained from step (ii) at $3^{rd}$ and $5^{th}$ position either simultaneously or sequentially;
iii. reducing compound obtained from step (ii) with reducing agent;
iv. selective deprotection of the compounds obtained from step (iii);
v. selective reduction of compound obtained from step (iv); to obtain protected (−) epicatechin or (+) epicatechin or mixture of two; and
vi. deprotection of the protected epicatechin to provide (−) epicatechin or (+) or mixture of two.

Quercetin [1] when treated with a protecting group such as benzyl bromide or benzyl chloride in presence of suitable base such as potassium carbonate in a suitable solvent such as dimethylformamide or NMP with or without any phase transfer catalyst such as TBAB, at temperature ranging from 0° C. to reflux can be converted to compound [2]. Compound [2] can be converted to compound [3] in presence of a protecting agent such as trimethylsilyl chloride in presence of a solvent such as DCM and/or THF with or without base such as DBU. Compound [3] can be selectively protected with a protecting group such as benzyl bromide as mentioned above to afford [4]. Compound [4] can be converted to mixture of compound [5]. and [6] i.e. 4H-chromene and 2H-chromene respectively in presence of a reducing agent such as lithium aluminium hydride in a solvent such as THF or ether at a temperature ranging from 0° C. to reflux. Compound [5] and [6] can be selectively deprotected to afford [7] in presence of a suitable reagent such as tetrabutyl ammonium bromide in a solvent such as THF or DCM. Compound [7] can be converted to compound [8] in presence of a reducing agent such as L-selectride in a solvent such as THF at a temperature ranging from −78° C. to ambient. Compound [8] when subjected to hydrogenation in presence of a catalyst such as palladium on carbon under hydrogen atmosphere at a temperature ranging from ambient to reflux can be converted to racemic epicatechin [9].

Synthetic Scheme 2:

As illustrated in Figure 2, the epicatechin is obtained by a process comprising the steps of:
  I. protecting the hydroxyl groups of quercetin using one or more achiral protecting groups;
  II. reducing the compound obtained from step (i);
  III. further reducing the compound obtained from step (ii) in the presence a chiral/achiral reducing agent;
  IV. deprotection of the compound obtained from step (iii) to provide (−) epicatechin or (+) or mixture of two.

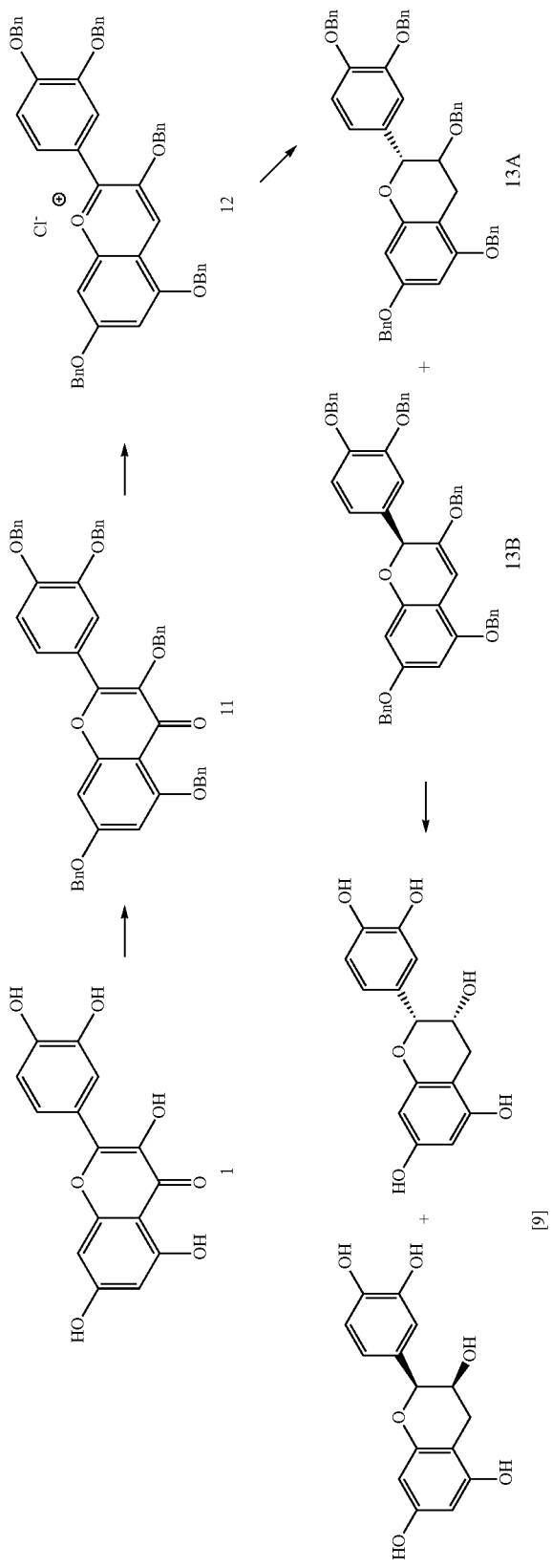

Quercetin [1] when treated with a protecting reagent such as benzyl bromide or benzyl chloride in presence of a base such as potassium carbonate in presence of a solvent such as dimethylformaide or NMP with or without any phase transfer catalyst such as TBAB at temperature ranging from 0° C. to reflux to obtain 3,5,7-tris(benzyloxy)-2-(3,4-bis(benzyloxy)phenyl)-4H-chromen-4-one [11]. Compound [11] can be converted into [12] in presence of a reducing agent such as vitride solution in presence of a solvent such as tetrahydrofuran or ether at a temperature ranging from 0° C. to reflux. Compound [12] can be converted to chiral/achiral 2H chromene analogs of formula 13A or 13B in presence of chiral/achiral reducing agents such as borohydride or boranes. [13A] or [13B] when subjected to hydrogenation in presence of a catalyst such as palladium on carbon under hydrogen atmosphere at a temperature ranging from ambient to 60° C. can be converted to chiral/achiral (+/-)-epicatechin [9]. The chiral/achiral reducing agent is selected from the group of lithium aluminium hydride, sodium borohydride, lithium borohydride, sodium cyanoborohydride, Wilkinson's catalyst, potassium borohydride, 9-Borabicyclo[3.3.1]nonane, Hantzsch Ester and (−) Diisopinocampheylborane. Hantzsch Ester exclusively provides 4H chromene whereas the use of 9-Borabicyclo[3.3.1]nonane(9-BBN) exclusively gives 2H chromene and thereby enantiomerically pure cis-epicatechin with either R,R-/(−) or S,S-/(+) configuration may be obtained by the process of the present invention.

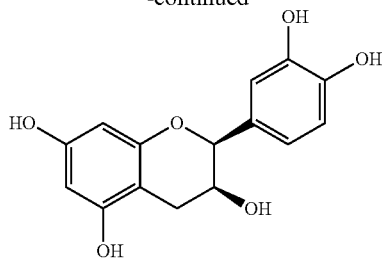

(+)epicatechin/
S,S-epicatechin

In an embodiment, the epicatechin may also be obtained from catechin by a process comprising the steps of:
  i. protecting the hydroxyl groups of any isomer of catechin in one or more steps using one or more achiral protecting groups;
  ii. hydroxylating the compound obtained from step (i);
  iii. dehydrating the compound obtained from step (ii) to obtain enantiomerically enriched protected epicatechin;
  iv. deprotection of the enantiomerically enriched protected epicatechin to provide (+/−)-epicatechin as a substantially pure enantiomer.

Synthetic Scheme 3:

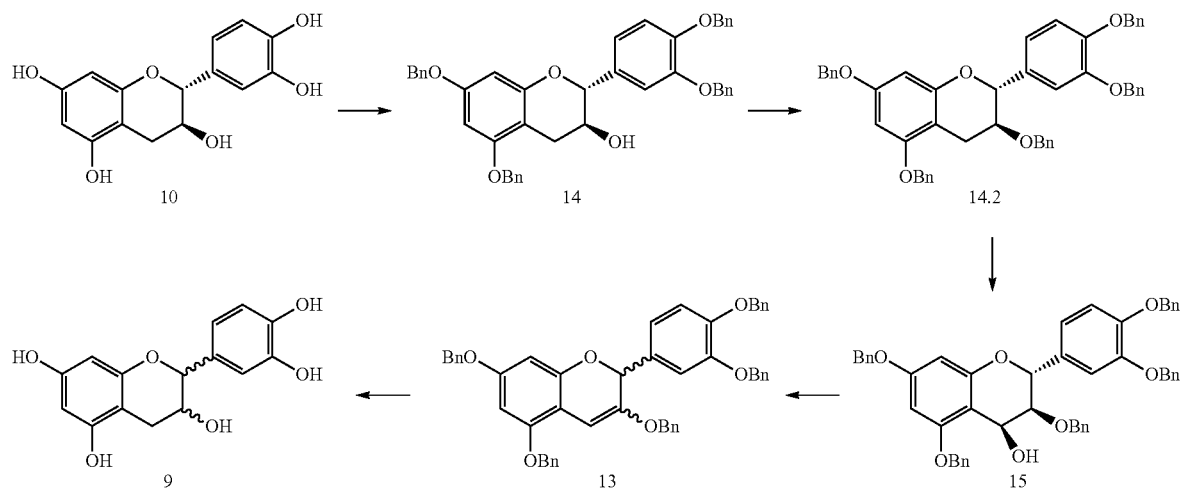

Catechin [10] can be converted to [14] by reacting with any protecting group known in literature such as benzyl bromide or benzyl chloride using a suitable base such as potassium carbonate or sodium hydride in a solvent such as DMF or NMP with or without any phase transfer catalyst such as TBAB at a temperature ranging from 0° C. to refluxing to yield [14.2]. Compound [14.2] can be converted to [15] using a hydroxylation reaction involving reagent such as DDQ in a solvent such as DCM and/or water at temperature ranging from ambient to refluxing. Compound [15] can be converted to compound [13] by elimination of water in presence of reagent such as MsCl and base such as triethylamine in a solvent such as dichloroethane at temperature ranging from ambient to refluxing. Compound [13] can be converted to epicatechin [9] by one pot hyderogantion and hyderogenolysis using reagent such as Pd/C in

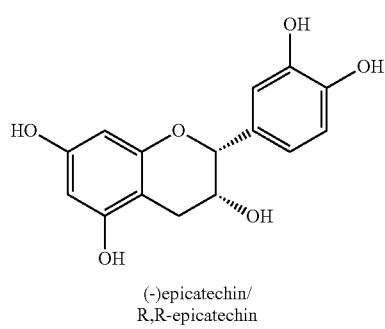

(−)epicatechin/
R,R-epicatechin solvent such as THF with or without additives such as acetic acid under hydrogen atmosphere at temperature ranging from ambient to 60° C.

As disclosed in the synthetic scheme 1, 2 and 3, the desired intermediates and the final product of the reaction, namely 2H chromene, 4H chromene, cynidin and epitehcin may be obtained by selective protection, reduction, hydroxylation and deprotection reactions.

In another aspect, the present invention is drawn to the intermediate compounds formed in the synthetic schemes as disclosed herein.

In another aspect, the present invention is directed to methods of preparing pharmaceutical or nutraceutical compositions comprising (+/−)-epicatechin. These methods comprise preparing epicatechin, or pharmaceutically acceptable salt(s) thereof, by the methods described herein and combining this with a pharmaceutically or nutraceutically acceptable carrier.

In a related aspect, the invention is directed to methods of administering such a pharmaceutical or nutraceutical composition to a subject in need thereof. Routes of administration for the pharmaceutical and nutraceutical compositions of the present invention include parenteral and enteral routes. Preferred enteral routes of administration include delivery by mouth (oral), nasal, rectal, and vaginal routes. Preferred parenteral routes of administration include intravenous, intramuscular, subcutaneous, and intraperitoneal routes.

Preferably, the pharmaceutical or nutraceutical compositions of the present invention are administered in an "effective amount." This term is defined hereinafter. Unless dictated otherwise, explicitly or otherwise, an "effective amount" is not limited to a minimal amount sufficient to ameliorate a condition, or to an amount that results in an optimal or a maximal amelioration of the condition. In the case when two or more pharmaceuticals are administered together, an effective amount of one such pharmaceutical may not be, in and of itself be an effective amount, but may be an effective amount when used together with additional pharmaceuticals.

The compounds of the present invention may be used for pharmaceutical, cosmetic, nutraceutical or food purposes. In addition, the compounds of the present invention may be used in regulation of mitochondrial dysfunction or mitochondrial depletion. Use of compounds of the present invention may be used for the activation mitochondrial biogenesis and functions.

Without being limited by theory the invention of the present application is amenable to commercial synthesis. The selective conversion of cyanidin to chiral 2H chromene or chiral 3 ketone is disclosed for the present application. This selective conversion enables synthesis of chiral 2H chromene which leads to synthesis of isomerically pure epi-catechin. The conversion of chiral catechin to chiral epicatechin involving chiral 2 H chromene as key intermediate is disclosed for the first time in the present invention.

While the invention has been described and exemplified in sufficient detail for those skilled in this art to make and use it, various alternatives, modifications, and improvements should be apparent without departing from the spirit and scope of the invention. The examples provided herein are representative of preferred embodiments, are exemplary, and are not intended as limitations on the scope of the invention. Modifications therein and other uses will occur to those skilled in the art. These modifications are encompassed within the spirit of the invention and are defined by the scope of the claims. It will be readily apparent to a person skilled in the art that varying substitutions and modifications may be made to the invention disclosed herein without departing from the scope and spirit of the invention.

Preparation of Epicatechin by Scheme-1

Synthesis of (−) & (+) Epicatechin consists of 6 steps, synthesis starts, from the benzylation of natural molecule Quercetin followed by the reduction and de-benzylation to get racemic Epicatechin and then (−) & (+) Epicatechin was produced by chiral separation from preparative HPLC.

EXAMPLE 1

Step 1: Preparation of 3',4',7-Tribenzylated Quercetin from Quercetin

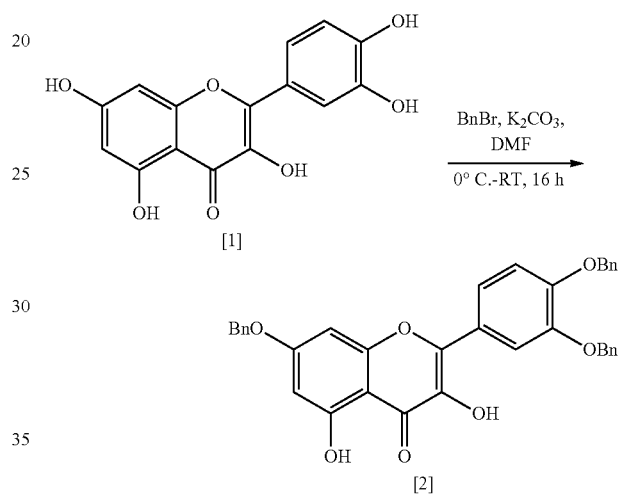

To a stirred of [1] (3.0 g, 9.9 mmol) in DMF was added $K_2CO_3$ (1.3 g, 29.7 mmol) at 0° C. under nitrogen atmosphere. After stirring at this temperature for 15 min, was added Benzyl bromide drop-wise. The temperature of reaction mixture was allowed to rise to room temperature and stirred it for overnight. TLC showed complete consumption of [1]. Reaction mixture was quenched with water (50 ml) and extracted with ethyl acetate (2×100 ml). The combined organic layer was washed with water, brine and dried over sodium sulphate. The organic layer was rotary evaporated to afford light brown sticky material. This crude product was loaded on to silica gel column and eluted with 8% ethyl acetate/hexane to afford yellowish green powder [2] (3.2 g, 57%). Analytical Data: ESIMS: 573[M$^+$+1]

Step 2: Protection of hydroxyl Group at $3^{rd}$ Position by TBDMS Group

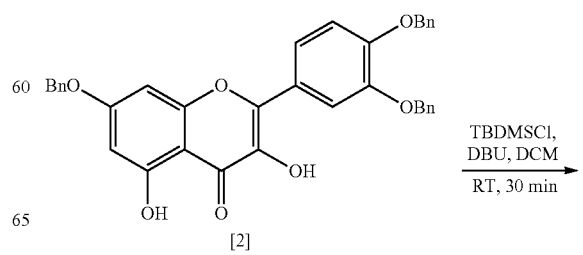

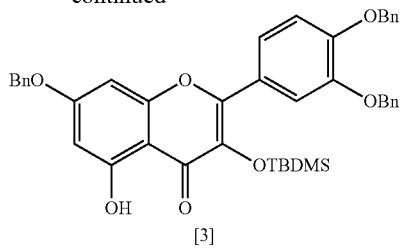

[3]

To a stirred of [2] (0.500 g, 0.87 mmol) in dry DCM (10 ml) was added DBU (1.5 ml) at RT under nitrogen atmosphere. After stirred at this temperature for 5 min, was added TBDMSCI dropwise (0.168 ml, 0.957 mmol) in DCM. The reaction mixture was allowed to stir at this temperature for 30 min. TLC showed complete consumption of [2]. Reaction mixture was quenched with addition of water (20 ml) and extracted with dichloromethane (2×100 ml). The combined organic layer was washed with water, brine and dried over sodium sulphate. The organic layer was rotary evaporated to afford light yellow sticky material (550 mg, 93%). This crude product was used as such for further steps.

Analytical Data: ESIMS: 687[M$^+$+1]

Step 3: Preparation of penta protected Quercetin [4]

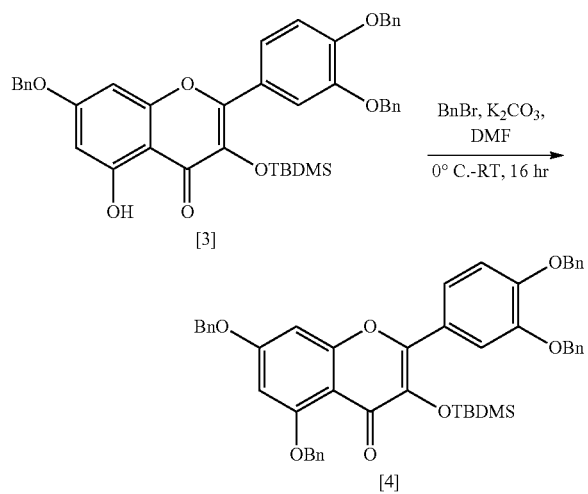

To a stirred of [3] (0.300 g, 0.43 mmol) in DMF was added K$_2$CO$_3$ (0.072 g, 0.52 mmol) at 0° C. under nitrogen atmosphere. After stirred at this temperature for 15 min, was added benzyl bromide (0.063 ml, 0.52 mmol) dropwise. The temperature of reaction mixture was allowed to rise to room temperature and stirred it for overnight. TLC showed complete consumption of [3]. Reaction mixture was quenched with water (20 ml) and extracted with ethyl acetate (2×100 ml). The combined organic layer was washed with water, brine and dried over sodium sulphate. The organic layer was rotary evaporated to afford light brown sticky material. This crude product was loaded on to silica gel column and eluted with 5% ethyl acetate/hexane to afford white solid powder [4] (0.300 g, 95%).

Analytical Data: ESIMS: 77[M$^+$+1]

Step 4: Synthesis of 4H and 2H Chromene from penta Protected quercetin [4]

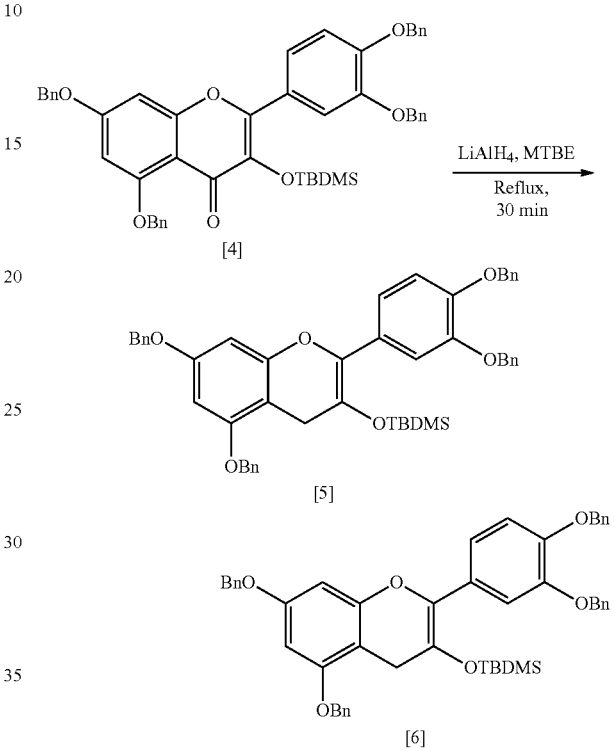

To a stirred suspension of [4] (0.300 g) in methyl tertiary butyl ether (10.0 ml) was added lithium aluminium hydride (0.052 g, 3.6 eq) in one portion at room temperature under nitrogen atmosphere. After stirring for 10 min at this temperature, temperature of reaction was raised to 65° C. to 70° C. After stirring at same temperature for 30 min, reaction mass was quenched with 1N HCl (10 ml) solution at 0° C.-5° C. then the temperature of reaction mass was raised to room temperature. Ethyl acetate (10 ml) was added to the reaction mass and stirred for 30 min, then organic layer was decanted, aqueous layer was diluted with ethyl acetate, filtered through celite bed, separated both aqueous and organic layers. Combined organic layers were concentrated under reduced pressure to afford light pink sticky material (0.220 g, 74%).

Analytical Data: ESIMS: 763[M$^+$+1]

Step 5: Synthesis of Ketone Intermediate [7]

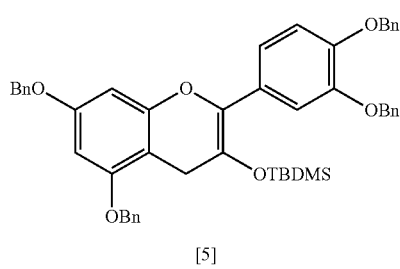

[5]

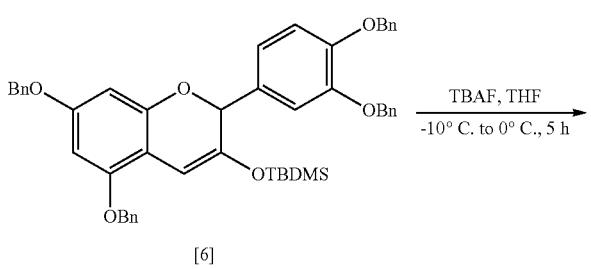

[6]

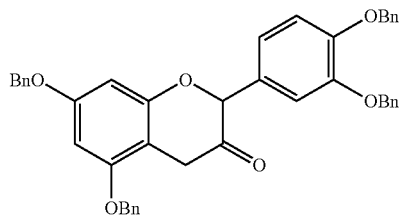

[7]

To a stirred solution of [5] and [6] in dry THF was added tetra-butyl ammonium bromide drop-wise at −10° C. under nitrogen atmosphere. The reaction mixture was allowed to stir at this temperature for 1 h, then the temperature was allowed to raise to 0° C. Reaction was monitored by TLC, till whole starting material gets consumed. After 5 h, reaction mixture was quenched by addition of saturated ammonium chloride and extracted with Ethyl acetate (2×50 ml). Combined organic layer was washed with brine and rotary evaporated to afford dark red sticky material. This crude material was used as such for further reaction.

Analytical Data:ESIMS: 649[M$^+$+1]

Step 6: Synthesis of Racemic tetrabenzylated epicatechin [8]

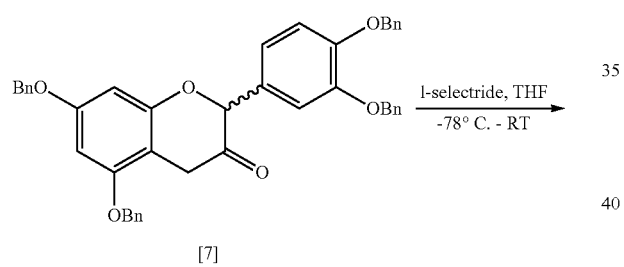

[7]

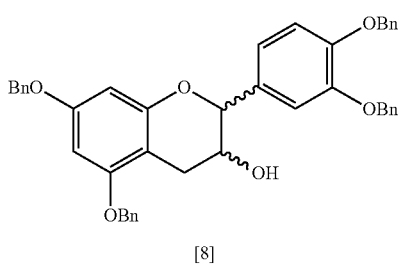

[8]

To a stirred solution of [7] (0.100 g) in dry THF at −78° C. was added L-selectride drop wise under nitrogen atmosphere. The resulting solution was stirred at −78° C. for 5 h and then the temperature of reaction mixture was allowed to come to room temperature. Reaction was monitored by TLC. After complete consumption of [7], saturated NaHCO$_3$ was added and extracted with ethyl acetate. The combined organic layer was washed with brine and dried over sodium sulphate and evaporated to afford the desired material (0.080 g 85%).

Analytical Data: ESIMS: 651[M$^+$+1]

Step 7:

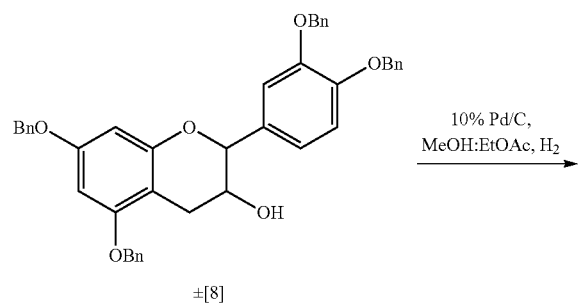

±[8]

To a stirred solution of [8] (0.180 g, 0.24 mmol) in 1:1 mixture ethyl acetate and methanol (8 ml), was added a slurry of 10% Pd/C (0.020 g) at room temperature. The reaction mixture was stirred at this temperature for 1 hr and then reaction temperature was raised to 50-55° C. and stirred at this temperature for overnight. The reaction mass was filtered over celite and the solvent was removed under rotary evaporator to afford light brown sticky material. This crude product was loaded on to silica gel column and eluted with 4% methanol/dichloromethane to afford off white powder [9] (0.045, 65%).

Analytical Data: ESIMS: 291[M$^+$+1]

Process of Preparation of Racemic Epicatechin

Synthesis of (−) & (+) Epicatechin consists of 4 steps as shown in scheme 2, synthesis starts from the benzylation of natural molecule Quercetin followed by the reduction and de-benzylation to get racemic tetrabenzylated epicatechin and then racemic epicatechin. The (+) and (−) isomer can be obtained by chiral separation using preparative chiral HPLC.

EXAMPLE 2

Step-1: Synthesis of Pentabenzylated quercetin from Quercetin using Benzyl chloride.

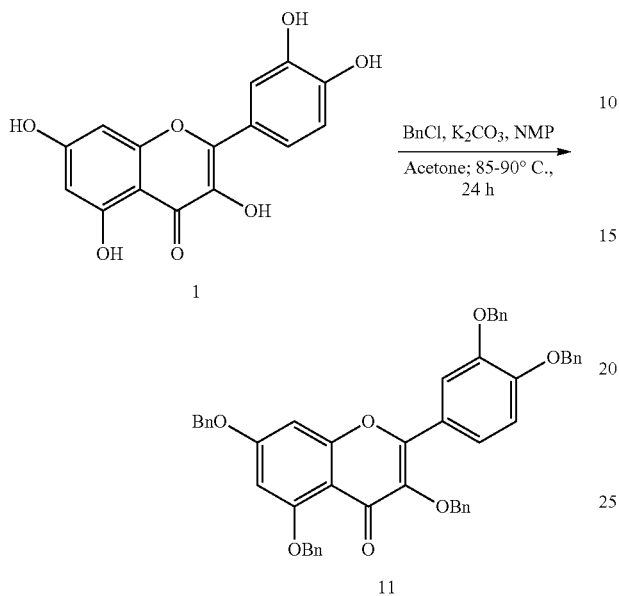

To a stirred solution of Quercetin dihydrate [1] (25 g, 0.074 mol) in N-methyl pyrrrolidone[NMP] (125 ml) and acetone (375 ml), potassium carbonate (122.5 gm, 0.89 mol) was added followed by slow addition of benzyl chloride (85.9 ml, 0.75 mol) and tetrabutyl ammonium bromide [TBAB] (1.19 gm, 3.7 mmol) at room temperature. The reaction mixture was heated at 85-90° C. and stirred for 24 hours. After completion of the reaction, acetone was evaporated and the reaction mass was cooled to 0-5° C. followed by addition of water (1250 ml) and the stirring was continued for an additional hour. The precipitated solid was filtered, washed three times with water and then 1:1 mixture of methanol: water to give 52 g (93%; HPLC purity-95%), off white colored desired product [2]

Analytical Data:
ESIMS: 753[M$^+$+1]:
1H NMR (300 MHz, CDCl3): δ (ppm) 7.72 (d, 1H, Ar—H); 7.60-7.62 (d, 1H, Ar—H); 7.14-7.50 (m, 25H, 5-Ar—H); 6.93 (d, 1H, Ar—H); 6.52 (d, 1H, Ar—H); 6.45 (d, 1H, Ar—H); 5.24-5.28 (s, 4H, 2×CH$_2$); 5.08-5.09 (s, 4H, 2×CH$_2$); 4.96 (s, 2H, CH$_2$).

Step-2: Synthesis of 4H and 2H Chromene from Pentabenzylated quercetin.

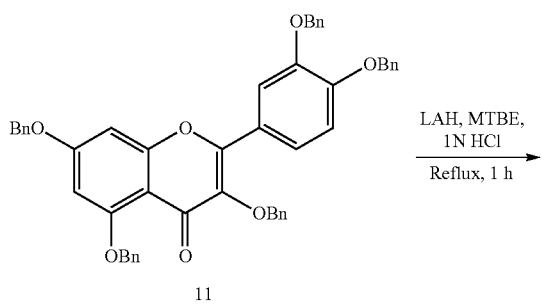

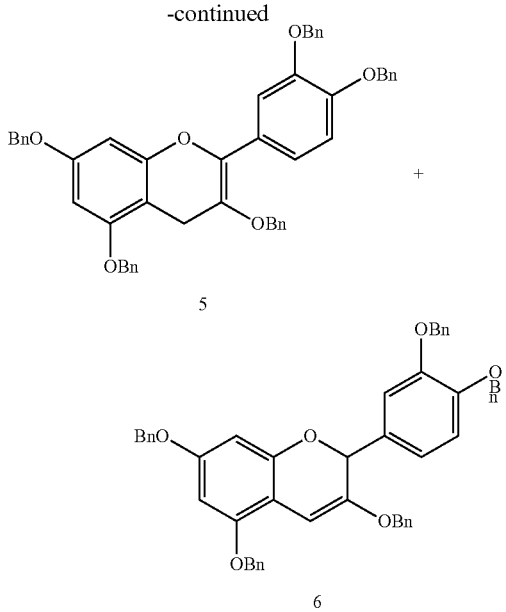

In a 4-neck 10000 mL RBF with thermometer pocket and nitrogen gas inlet, MTBE (6000 mL), [2] (200 g, 0.266 mol) and LAH (36.4 g, 0.957 mol) were charged under inert atmosphere at 25° C.-30° C. The resulting reaction mixture was heated to 55° C.-60° C. and stirred for 1 h and reaction progress was monitored by TLC. After completion consumption of starting material, the reaction mixture was cooled to 0° C.-5° C. then quenched with 1N HCl (800 mL). Reaction mass temperature was raised to 25° C.-30° C. and diluted with EtOAc (1000 ml) stirred for 30 min. Organic layer was separated. The crude aluminate complex was diluted with EtOAc (2000 mL) and filtered through celite bed and bed was washed with EtOAc (1000 mL), separated both the organic and aqueous layers, combined organic layers were concentrated under vacuum at 50° C. to get the crude compound as an off—white solid (200 g). Crude compound (200 g) was triturated with EtOAc (1000 mL) for 4 h at 25° C.-30° C. then solid was filtered and washed with EtOAc (500 ml). Wet cake was dried under vacuum at RT for 4 h to give [3] (80.0 gm, 41%) as an off-white solid.

After isolation of [3] ML's was concentrated under reduced pressure pale yellow color residue was obtained that residue was seeded with [4] (10 mg) then left it for overnight at RT. Off white color semi solid formation was observed, the obtained semi solid was triturated with 50% EtOAc: hexane (1000 ml) for 30 min at RT, solid was filtered and washed with 50% EtOAc: hexane (1000 ml). Wet cake was dried under vacuum at RT for 4 h to get [4] (60.0 gm, 31%) as an off-white solid.

Analytical Data:
ESIMS: 739[M$^+$+1]
1H NMR (300 MHz, CDCl3) [3]: δ (ppm) 7.53-7.54 (d, 1H, J=2.1 Hz), 7.26-7.46 (m, 25H), 6.91-6.94 (d, 1H, J=9 Hz); 6.25-6.91 (2H, m), 5.190 (1H, s), 4.982-5.133 (6H, m), 4.735 (2H, s), 3.62 (s, 2H).

1H NMR (300 MHz, CDCl3) [4]: δ (ppm) 7.53-7.54 (d, 1H, J=2.1 Hz); 7.26-7.46 (m, 25H); 6.91-6.94 (d, 1H, J=9 Hz); 6.14-6.23 (m, 2H); 6.01 (s, 1H), 5.6 (s, 1H), 4.882-5.137 (m, 10H).

Step-3: Synthesis of Racemic Epicatechin from 4H-Chromene:

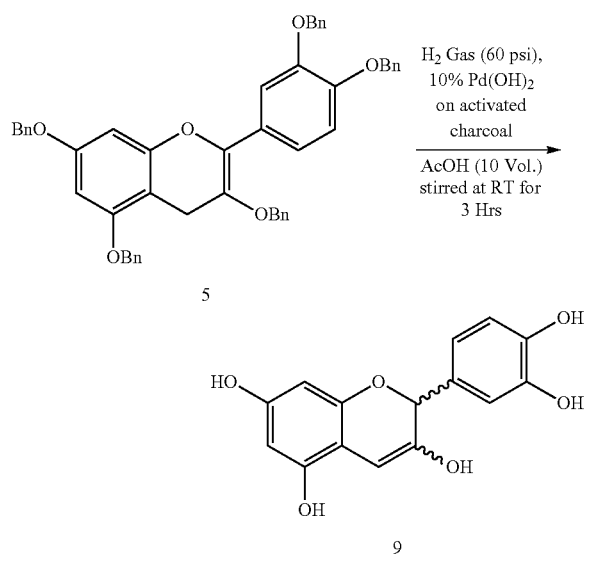

To a slurry of glacial acetic acid (50 ml) and 10% Pd(OH)$_2$ on activated charcoal (1.25 gm) in hydrogen Parr Glass vessel flask (500 ml), Compound[3] (5 gm, 6.7 mMol) was added under nitrogen atmosphere. The resultant solution was stirred under hydrogen pressure (40-60 psi) at room temperature for 3 h. After completion of reaction, reaction mixture was filtered through Celite bed and washed with methanol under suction and concentration of the filtrate via toluene azeotrope to get the crude solid material (2.2 gm, 110%). The solid was column chromatographed on Silica gel (100-200 Mesh) by using Dichloromethane/Methanol as mobile phase to get [5] (1.6 gm, 82%; HPLC purity 96%).

Analytical Data:
ESIMS: 291 [M$^+$+1]
$^1$H-NMR (D$_6$-DMSO, 300 MHz): δ (ppm) 9.2 (s, 1H), 8.90 (s, 1H), 8.81 (s, 1H),8.72 (s, 1H) 6.88 (s, 1H), 6.65 (s, 2H), 5.88 (d, 1H, J=2.1), 5.71 (d, 1H, J=2.4 Hz), 4.722 (b, 1H), 4.656-4.672 (d, 1H, J=4.8 Hz), 3.971-3.992 (m, 1H), 2.37-2.7 (dd, 2H).

Step-4: Chiral Preparative HPLC Resolution of Racemic Epicatechin:

Analytical HPLC method of separation:

The racemic mixture of Epicatechin was dissolved in methanol and checked for its chiral purity on reverse phase CHIRAL PAK® IC (250×4.6) mm, 5μ column at 25 0 C temperature. The mobile phase used was hexanes/ethanol/trifluoroacetic acid//60/40/0.05 (v/v/v) with a flow rate of 1.0 ml/minute and sample injection volume of 10 μl. The signals were monitored at UV 280 nm with PDA. The both isomers separated with a retention time difference of about 1.6 minutes. The faster moving isomer on HPLC eluted at 4.7 minute while the slower moving isomer came at 6.3 minute on a 15 minute run. Assignment of absolute configuration to the either of the resolved isomers was done based on retention time of the two enantiomers of the racemic epicatechin synthesized compared with the retention time of the commercially available natural epicatechin (2R,3R) under similar HPLC conditions. Based on the retention time, the slow moving isomer eluted at 6.3 minutes was assigned to be (−)-epicatechin ((2R,3R)-2-(3,4-Dihydroxyphenyl)-3,4-dihydro-1(2H)-benzopyran-3,5,7-triol) isomer and the fast moving isomer which eluted at 4.7 minutes was assigned to be (+)-epicatechin (((2S,3S)-2-(3, 4-Dihydroxyphenyl)-3,4-dihydro-1(2H)-benzopyran-3,5,7-triol) isomer.

Preparative HPLC Method of Separation:

The racemic mixture (0.200 g) was dissolved in methanol and separated on a preparative HPLC on CHIRAL PAK® IC (250×20) mm column at 25° C. temperature. The sample injection volume was 2.0 ml with a feed concentration of 5 mg/ml. The mobile phase used was Hexanes/EtOH//60/40 v/v with a flow rate of 18 ml/minute. The detection was done at UV 280 nm with PDA. The faster moving (+) Epicatechin isomer I (0.085 g; Chiral purity by HPLC >99%) eluted at 4.7 minute and the slower moving (−) Epicatechin isomer II (0.084 g; Chiral Purity by HPLC >99%) at 6.3 minute.

EXAMPLE 3

Step 1:

To a stirred of [1] (3.0 g, 9.9 mmol) in DMF was added K$_2$CO$_3$ (1.3 g, 49.5 mmol) at 0° C. under nitrogen atmosphere. After stirring at this temperature for 15 min, was added Benzyl bromide drop-wise. The temperature of reaction mixture was allowed to rise to room temperature and stirred it for overnight. TLC showed complete consumption of [10]. Reaction mixture was quenched with water (50 ml) and extracted with ethyl acetate (2×100 ml). The combined organic layer was washed with water, brine and dried over sodium sulphate. The organic layer was rotary evaporated to afford light brown sticky material. This crude product was loaded on to silica gel column and eluted with 8% ethyl acetate/hexane to afford yellowish green powder [11] (3.2 g, 57%).

Analytical Data: ESIMS: 753 [M$^+$+1]

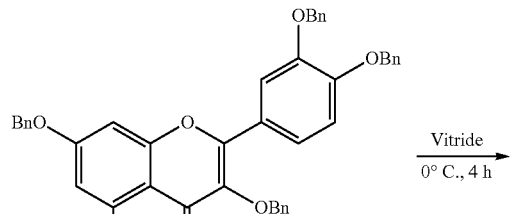

11

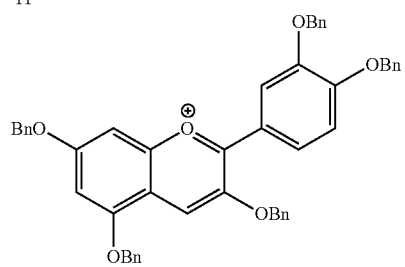

12

Step 2:

To a stirred solution of [11] (25 g, 0.0332 mol) in dry tetrahydrofuran under nitrogen atmosphere was added Vitride solution (56 ml, 0.166 ml) at 0-5° C. over a period of 5 min. The reaction was stirred at this temperature for 4 h. After completion of reaction the reaction mixture was quenched with saturated NaCl solution under cooling. Reaction mixture was further diluted with ethyl-acetate, organic layer was separated, dried over sodium sulfate and evaporated under reduced pressure to give crude pale yellow gummy mass (30.0 g). The above crude mass was purified by column chromatography on silica using ethyl acetate/hexane as eluent to afford yellow gummy mass (15.0 g) which was further treated with methanolic HCl at 0-5° C. for 2 h and then at 25-30° C. for 24 h. The wet cake thus obtained was dried under vacuum to afford [12] as a pinkish solid (55%).

Analytical Data: ESIMS: 738[M$^+$+1]

Step 3:

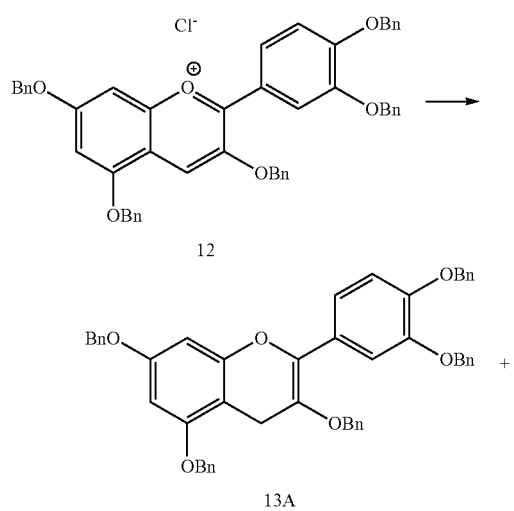

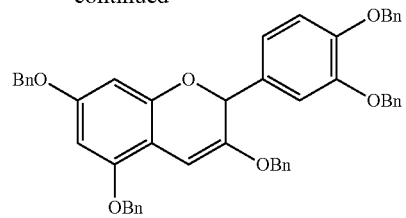

13B

To a stirred solution of [12] in suitable solvents such dry tetrahydrofuran, dichloromethane, ethyl acetate under nitrogen atmosphere was added reducing agents mentioned in Table 1. [12] can also be converted to chiral 2H-chromene [13B] in presence of suitable chiral reducing agents such as borane preferably 'S' or 'R.' alpine borane or (−) Diisopinocampheylborane. Chiral or achiral [13B] when subjected to hydrogenation in presence of palladium in hydrogen atmosphere afforded chiral or achiral epicatehcin [9] as major product.

TABLE 1

Example conditions to yield 2H and/or 4H Chromene

| Starting material | Reducing agents | Ratio 13A:13B |
|---|---|---|
| [12] | NaCNBH$_3$, | 2:1 |
| [12] | Willkinsons catayst, | 1:2 |
| [12] | LAH | 0:1 |
| [12] | NaBH$_4$ | 1:2 |
| [12] | LiBH$_4$ | 1:1 |
| [12] | KBH$_4$ | 1:1 |
| [12] | 9-BBN | 0:1 |
| [12] | Hantzsch Ester | 1:0 |
| [12] | (-)Diisopinocampheylborane | 1:1 |

Step 3A:

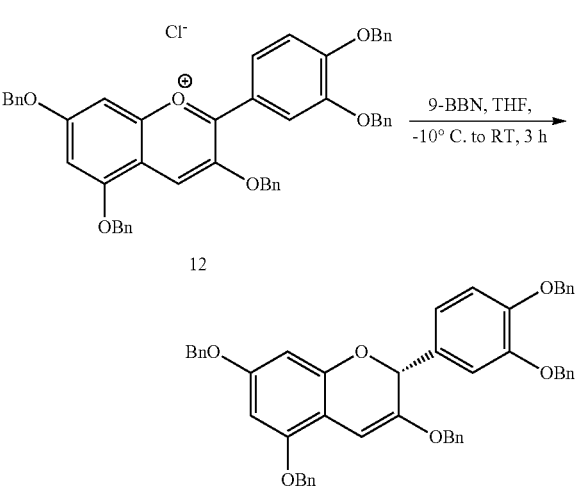

To a stirred solution of [12] (0.5 g, 0.67 mmol) in dry tetrahydrofuran under nitrogen atmosphere was added 9-BBN (0.5M/THF) (3.3 ml 1.69 mmol) at −10° C. over a period of 5 min. The reaction was stirred at this temperature for 1 h and then temperature was raised to room temperature and allowed to stirred at this temperature for 12 h. After completion of reaction, the reaction mixture was quenched with water under cooling. Reaction mixture was further diluted with ethyl-acetate, organic layer was separated, dried over sodium sulfate and evaporated under reduced pressure to give crude light pink gummy mass (0.5 g). The above crude mass was purified by column chromatography on silica using ethyl acetate/hexane as eluent to afford [13B] as light pink sticky material (0.35 g, 70%).

Analytical Data: ESIMS: 738[M$^+$+1]

Step 3B:

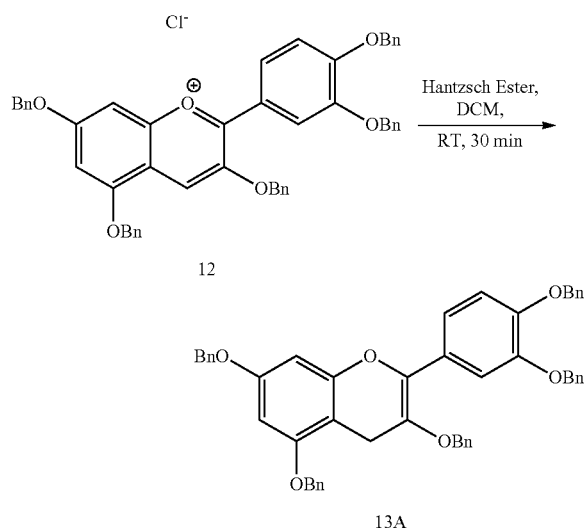

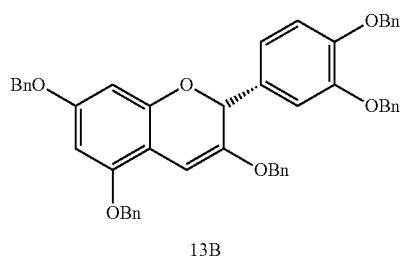

13B

To a stirred solution of [12] (0.1 g, 0.12 mmol) in dry tetrahydrofuran under nitrogen atmosphere was added (−) Diisopinocampheylborane (0.03 g, 0.12 mmol) at −40° C. over a period of 5 min. The reaction was stirred at this temperature for 2 h. TLC showed complete consumption of [12]. Reaction mixture was then quenched with water and diluted with ethylacetate, organic layer was separated, dried over sodium sulfate and evaporated under reduced pressure to give 1:1 mixture of [13A] and chiral [13B] as light pink sticky material (0.06 g, 70%).

Analytical Data: ESIMS: 738[M$^+$+1]

EXAMPLE 4

Step 1:

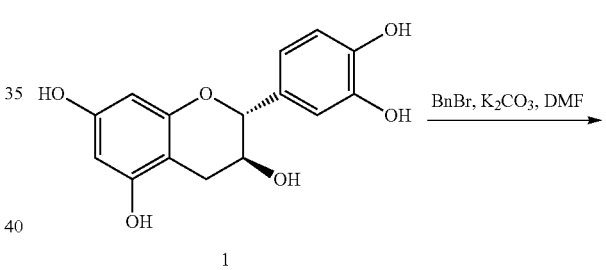

To a stirred solution of [12] (0.1 g, 0.12 mmol) in dry dichloromethane under nitrogen atmosphere was added Hantzsch ester (0.03 g, 0.14 mmol) in one portion at room temperature. Reaction mixture was allowed to stirred at this temperature for 15 min. After completion of reaction, the reaction mixture was quenched with water under cooling. Reaction mixture was further diluted with dichloromethane, organic layer was separated, dried over sodium sulfate and evaporated under reduced pressure to give [13A] as light pink sticky material (0.07 g, 85%).

Analytical Data: ESIMS: 738[M$^+$+1]

Step 3C:

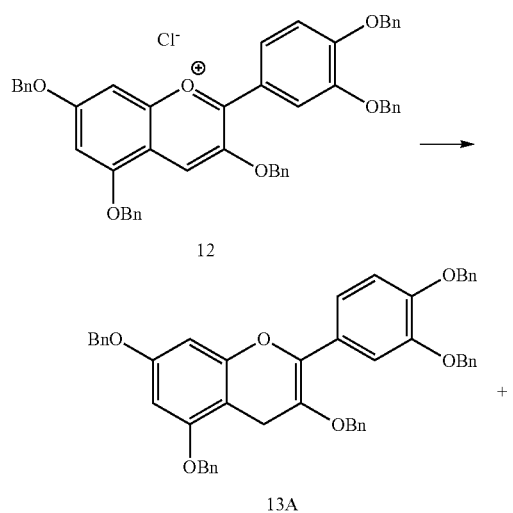

To a stirred of [10] (1.0 gm, 3.4 mmol) in DMF was added K$_2$CO$_3$ (2.3 gm, 17.0 mmol) at 0° C. under nitrogen atmosphere. After stirring at this temperature for 15 min, was added Benzyl bromide drop-wise. The temperature of reaction mixture was allowed to raise to room temperature and stirred it for overnight. TLC showed complete consumption of [10]. Reaction mixture was quenched with water (50 ml) and extracted with ethyl acetate (2×100 ml). The combined organic layer was washed with water, brine and dried over sodium sulphate. The organic layer was rotary evaporated to afford light brown sticky material. This crude product was loaded on to silica gel column and eluted with 8% ethyl acetate/hexane to afford white powder [14] (1.5 gm, 68%).
Analytical Data: ESIMS: 651[M$^+$+1]

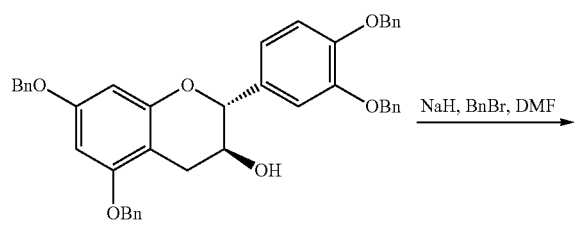

14

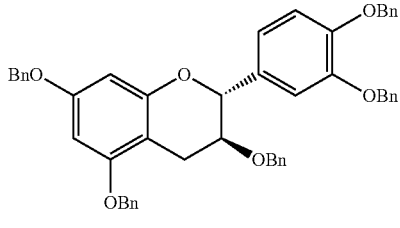

14.2

Step 2:
To a stirred of [14] (1.5 gm, 2.3 mmol) in DMF was added NaH portionwise (0.85 gm, 3.4 mmol) at 0° C. under nitrogen atmosphere. After stirring at this temperature for 15 min, was added Benzyl bromide drop-wise. The temperature of reaction mixture was allowed to raise to room temperature and stirred it for overnight. TLC showed complete consumption of [14]. Reaction mixture was quenched with water (50 ml) and extracted with ethyl acetate (2×100 ml). The combined organic layer was washed with water, brine and dried over sodium sulphate. The organic layer was rotary evaporated to afford light brown sticky material. This crude product was loaded on to silica gel column and eluted with 8% ethyl acetate/hexane to afford white sticky material [14.2] (1.4 gm, 82%).
Analytical Data: ESIMS: 741 [M$^+$+1]

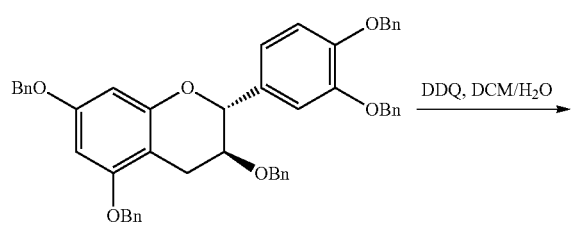

14.2

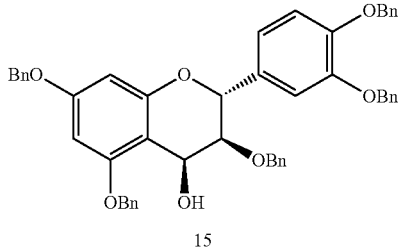

15

Step 3:
A solution of 14.2 (1.0 gm, 1.3 mmol) and DDQ (370 mg, 5.2 mmol) in a mixture of CH$_2$Cl$_2$ (15 ml) and H$_2$O (6.0 ml) was vigorously stirred for 3 h at room temperature. To the reaction mixture was added saturated aqueous NaHCO$_3$ and extracted with CH$_2$Cl$_2$ (3×130 mL). The combined extracts were dried over anhydrous MgSO$_4$ and evaporated in vacuo. The residue was purified by flash chromatography (AcOEt-CHCl$_3$ 1:40) to give [15] (0.6 gm, 60%) as a white powder.
Analytical Data: ESIMS: 757[M$^+$+1]

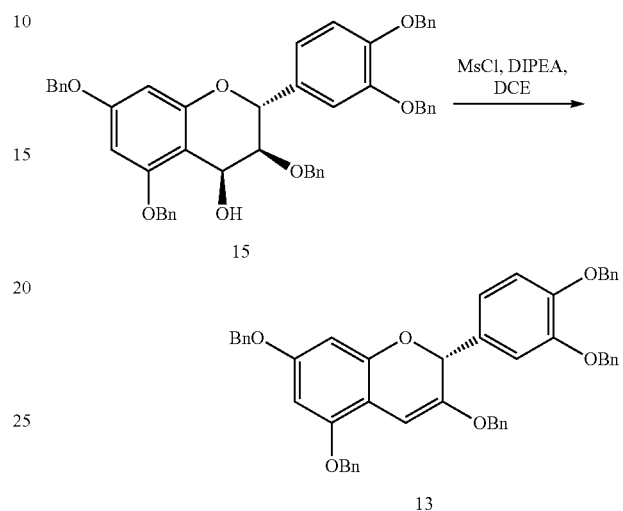

15

13

Step 4:
To a solution of [15] (200 mg, 0.24 mmol) and DIPEA (0.72 mmol) in 1,2-dichloroethane (10 mL) was added MsCl (0.72 mmol) at room temperature. The reaction mixture was allowed to heat at 80° C. and stirred for 6.0 h. After cooling the reaction was quenched by addition of a saturated aqueous NaHCO$_3$ (40 mL) and the mixture was extracted with AcOEt (3×40 mL). The combined extracts were dried over anhydrous MgSO$_4$, evaporated in vacuo, and purified by flash column chromatography to give [13] (0.15 gm, 75%) as sticky light brown material.
Analytical Data: ESIMS: 738[M$^+$+1]
Step 5:

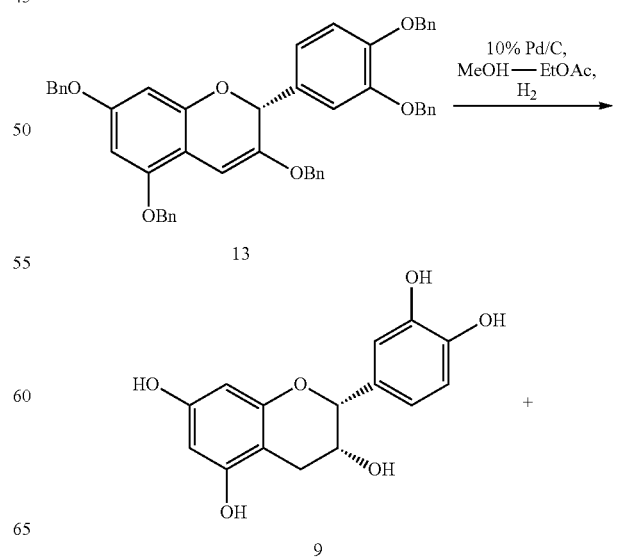

13

9

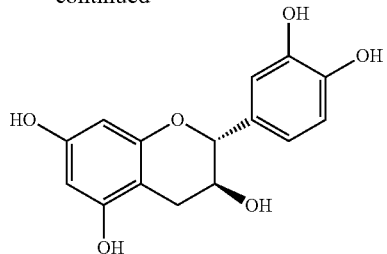

TO a stirred solution of [13] (0.180 gm, 0.24 mmol) in 1:1 mixture ethyl acetate and methanol (8 ml), was added a slurry of 10% Pd/C (0.020 gm) at room temperature. The reaction mixture was stirred at this temperature for 1 hr and then reaction temperature was raised to 50° C.-55° C. and stirred at this temperature for overnight. The reaction mass was filtered over celite and the solvent was removed under rotary evaporator to afford light brown sticky material. This crude product was loaded on to silica gel column and eluted with 4% methanol/Dichloromethane to afford off white powder [9](0.04 gm, 55%) along with some catechin.

Analytical Data: ESIMS: 291[M$^+$+1]

Advantages of the Invention

1. The present invention provides a process of synthesis of cis-epicatechin in isomerically pure, isomerically enriched and/or racemic forms.
2. The present invention provides novel intermediates in isomerically pure, isomerically enriched and/or racemic forms which can be converted to epicatechin.
3. The process of the present application has increased yield over other processes of prior art.
4. The process of the present invention is amenable for large scale commercial production.

We claim:

1. A process for synthesis of enatiomerically pure epicatechin, or enatiomerically enriched epicatechin, or a racemic mixture of (+) and (−) epicatechin, or its intermediates, comprising:
   I. obtaining penta-protected quercetin in one or more than one selective protection steps;
   II. reducing the penta-protected quercetin obtained from step I;
   III. optionally deprotecting the compound of step II;
   IV. reducing the compound obtained from step II or step III in the presence of a chiral/achiral reducing agent to obtain a chiral intermediate; and
   V. deprotecting and/or hydrogenating the chiral intermediate obtained from step IV to obtain (−)-epicatechin; or
   VI. optionally simultaneously deprotecting and hydrogenating the compound obtained from step II to obtain racemic epicatechin.

2. The process of claim 1, wherein the selective protection of the hydroxyl groups is carried out in the presence of
   a protecting agent selected from allyl bromide, propargyl bromide, benzyl bromide, benzyl chloride, 2-fluoroethyl bromide, 4-nitrobenzyl bromide, 4-chlorobenzyl bromide, 4-methoxybenzyl bromide, a-bromo-p-tolunitrile, cinnamyl bromide, methyl 4-bromocrotonate, crotyl bromide, 1-bromo-2-pentene, 3-bromo-1-propenyl phenyl sulfone, 3-bromo-1-trimethyl silyl-1-propyne, 3-bromo-2-octyne, 1-bromo-2-butyne, 2-picolyl chloride, 3-picolyl chloride, 4-picolyl chloride, 4-bromomethyl quinoline, bromoacetonitrile, epichlorohydrin, bromofluoromethane, bromonitromethane, methyl bromoacetate, methoxymethyl chloride, bromoacetamide, 2-bromoacetophenone, 1-bromo-2-butanone, bromo chloromethane, bromomethyl phenyl sulfone, 1,3-dibromo-1-propene, trimethyl silyl chloride, and tert-butyldimethylsilyl chloride,
   a base selected from an alkali metal hydride, a dialkylamide, a bis(trialkylsilyl)amide, diazabicycloundecene, an alkali metal carbonate, and an alkali metal hydroxide, and a polar organic solvent selected from acetone, acetonitrile, tetrahydrofuran, ethyl acetate, dioxane, N,N-dimethylformamide, dichloromethane, a sulfoxide, and N-methylpyrrolidinone, or a mixture thereof,
   at atmospheric pressure, at a temperature in the range of 0-80° C.

3. The process of claim 1, wherein the reduction of step II is carried out in the presence of a reducing agent selected from sodium amalgam, zinc mercury amalgam, a metal hydride, and vitride solution, with or without a Lewis acid selected from aluminum chloride, cerium chloride, zinc chloride, boron trifluoride, and iodine.

4. The process of claim 1, wherein the chiral/achiral reducing agent of step IV is selected from sodium borohydride, sodium cyanoborohydride, potassium borohydride, lithium borohydride, 9-Borabicyclo[3.3.1]nonane, 'S' or 'R' alpine borane, (−) diisopinocampheylborane, L-selectride, Wilkinson's catalyst, 2,3-dichloro-5,6-dicyano-1,4-benzoquinone, Hantzsch Ester, aluminum hydride, diisobutyl aluminum hydride, trialkoxy aluminum hydride and sodium bis(2-methoxy ethoxy) aluminum hydride.

5. The process of claim 1, wherein deprotection and/or hydrogenation of step V is performed using hydrogen gas in the presence of a hydrogenation catalyst adsorbed onto a solid support, and a solvent or a mixture of solvents at a temperature in the range of 20-60° C.,
   wherein
   the hydrogenation catalyst is selected from platinum, palladium, and nickel; and
   the solvent is selected from methanol, ethanol, ethyl acetate, tetrahydrofuran, and acetic acid, or mixtures thereof.

6. The process of claim 1, comprising:
   i. selectively protecting Quercetin at its 7, 3' and 4' positions;
   ii. protecting the hydroxyl groups of the compound obtained from step (i) at its 3 and 5 positions, either simultaneously or sequentially;
   iii. reducing the compound obtained from step (ii) with a reducing agent;
   iv. selectively deprotecting the compounds obtained from step (iii);
   v. selectively reducing the compound obtained from step (iv), thereby obtaining protected (−) epicatechin or (+) epicatechin or a mixture of the two; and
   vi. deprotecting the protected epicatechin to provide (−) epicatechin or (+) epicatechin or a mixture of the two.

7. The process of claim 6, comprising:
   i. treating quercetin with benzyl bromide in the presence of potassium carbonate and DMF or acetone to obtain a compound of formula [2];

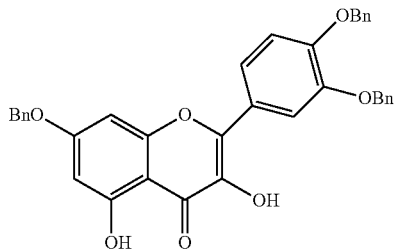

2 ii-a. protecting the hydroxyl group at the 3-position of the compound of formula [2] with TBDMS in the presence of a solvent selected from DCM and THF, with or without a base to obtain a compound of formula [3];

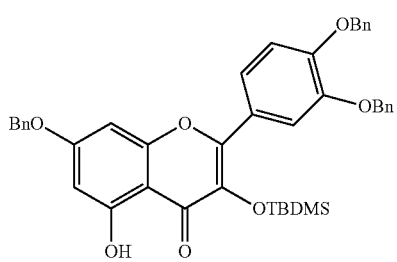

3 ii-b. protecting the hydroxyl group of the compound of formula [3] with benzyl bromide in the presence of potassium carbonate and DMF or acetone to obtain a compound of formula [4];

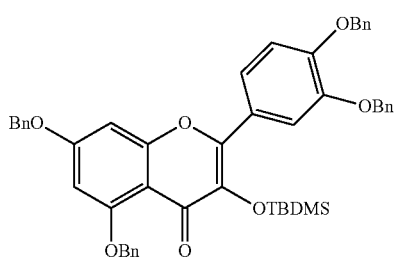

4 iii. reducing the compound of formula [4] with LiAlH$_4$ in the presence of a solvent to obtain a mixture comprising a compound of formula [5] and a compound of formula [6];

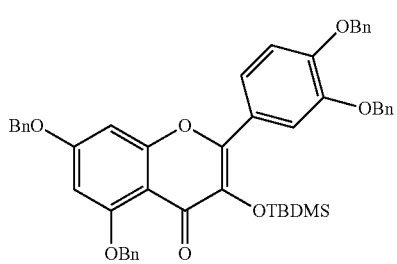

5

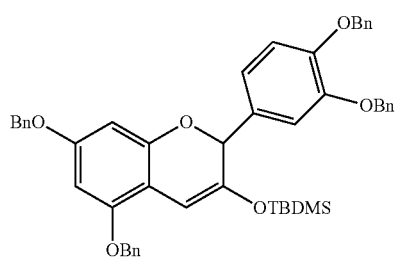

6 iv. deprotecting the compounds of the mixture obtained in step (iii) at their 3 position with tetrabutyl ammonium bromide under nitrogen atmosphere to obtain a compound of formula [7];

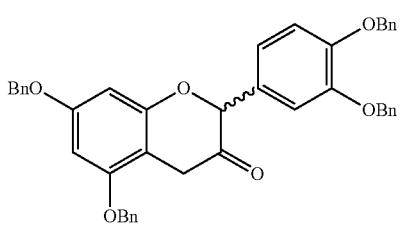

7 v. reducing the compound of formula [7] in the presence of L-selectride in dry THF at −78° C. under nitrogen atmosphere to obtain a chiral intermediate; and vi. hydrogenating the chiral intermediate of step (v) in presence of palladium on carbon under hydrogen atmosphere at a temperature ranging from ambient to 60° C. to obtain (−) epicatechin or (+) epicatechin or a mixture of the two.

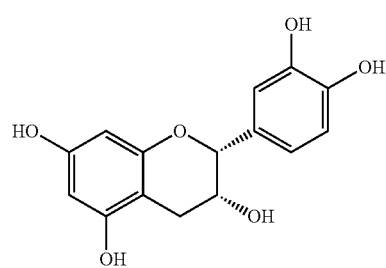

(−)epicatechin

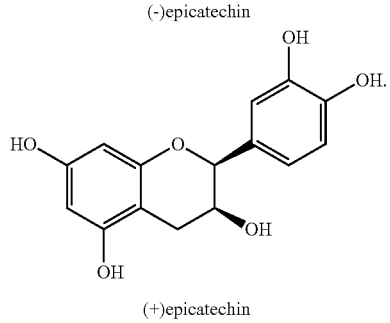

(+)epicatechin

8. The process of claim 1, comprising:
   i. protecting the hydroxyl groups of Quercetin using one or more achiral protecting groups;
   ii. reducing the compound obtained from step (i);

iii. further reducing the compound obtained from step (ii) in the presence of a chiral/achiral reducing agent;

iv. deprotecting the compound obtained from step (iii) to provide (−) epicatechin or (+) epicatechin or a mixture of the two.

9. The process of claim 1, comprising:

i. treating quercetin with benzyl bromide in the presence of potassium carbonate in a mixture of NMP and acetone to obtain 3,5,7-tris(benzyloxy)-2-(3,4-bis(benzyloxy)phenyl)-4H-chromen-4-one of formula [11];

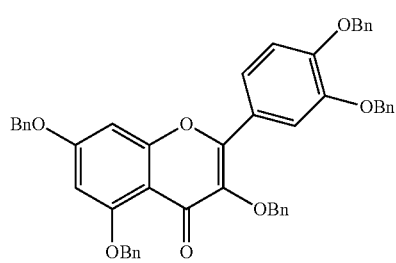

11 ii. reducing the compound of formula [11] in the presence of vitride solution in the presence of a solvent to obtain compound of formula [12]

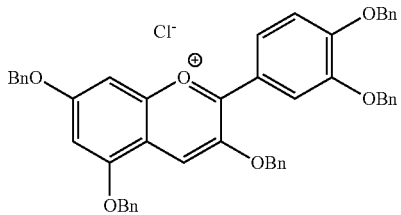

12 iii. reducing the compound of formula [12] in the presence of a chiral/achiral reducing agent to obtain a compound of formula [13A] or a compound of formula [13B] or a mixture of the two, wherein the chiral/achiral reducing agent is selected from lithium aluminium hydride, sodium borohydride, lithium borohydride, sodium cyanoborohydride, Wilkinson's catalyst, potassium borohydride, 9-borabicyclo[3.3.1]nonane, Hantzsch Ester, and (−) diisopinocampheylborane;

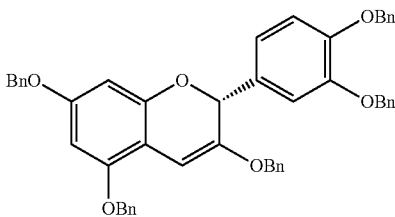

13A

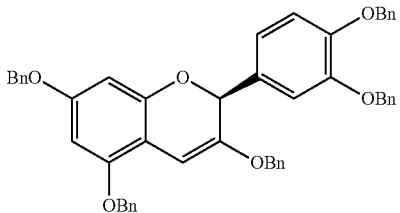

13B iv. hydrogenating the compound of formula [13A] or the compound of formula [13B] or the mixture of the two in the presence of palladium on carbon under a hydrogen atmosphere at a temperature ranging from ambient to 60° C. to obtain (+) epicatechin or (−) epicatechin or a mixture of the two

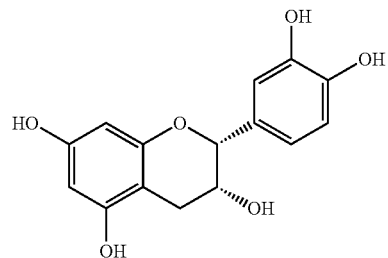

(−)epicatechin

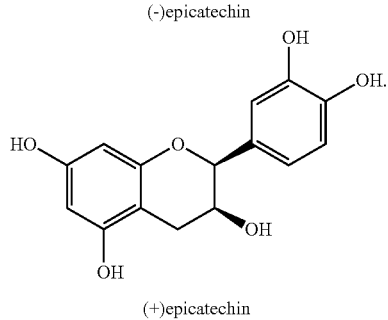

(+)epicatechin

* * * * *

UNITED STATES PATENT AND TRADEMARK OFFICE
CERTIFICATE OF CORRECTION

PATENT NO. : 9,556,140 B2
APPLICATION NO. : 14/763018
DATED : January 31, 2017
INVENTOR(S) : Dugar et al.

It is certified that error appears in the above-identified patent and that said Letters Patent is hereby corrected as shown below:

In the Claims

At Column 39, Line 62, please replace:
"bromide, 4-methoxybenzyl bromide, a-bromo-p-toluni-"
With:
-- bromide, 4-methoxybenzyl bromide, α-bromo-p-toluni- --

At Column 39, Line 65, please replace:
"phenyl sulfone, 3-bromo-1-trimethyl silyl-1-propyne,"
With:
--phenyl sulfone, 3-bromo-1-trimethylsilyl-1-propyne,--

At Column 40, Lines 28-33, please replace:
"lithium borohydride, 9-Borabicyclo[3.3.1]nonane, 'S' or 'R' alpine borane, (-) diisopinocampheylborane, L-selectride, Wilkinson's catalyst, 2,3-dichloro-5,6-dicyano-1,4-bcnzo-quinone Hantzsch Ester, aluminum hydride, diisobutyl aluminum hydride, trialkoxy aluminum hydride and sodium bis(2-methoxy ethoxy) aluminum hydride."
With:
--lithium borohydride, 9-borabicyclo[3.3.1]nonane, 'S' or 'R' alpine borane, (-) diisopinocampheylborane, L-selectride, Wilkinson's catalyst, 2,3-dichloro-5,6-dicyano-1,4-benzo-quinone Hantzsch Ester, aluminum hydride, diisobutylaluminum hydride, trialkoxyaluminum hydride and sodium bis(2-methoxyethoxy) aluminum hydride.--

Signed and Sealed this
Twentieth Day of February, 2018

Andrei Iancu
*Director of the United States Patent and Trademark Office*

At Column 40, Line 34, please replace:
"5. The process of claim 1, wherein deprotection and/or"
With:
--5. The process of claim 1, wherein the deprotection and/or--

At Column 41, Lines 50-66, please replace:
"iii. reducing the compound of formula [4] with LiAlH$_4$ in the presence of a solvent to obtain a mixture comprising a compound of formula [5] and a compound of formula [6];

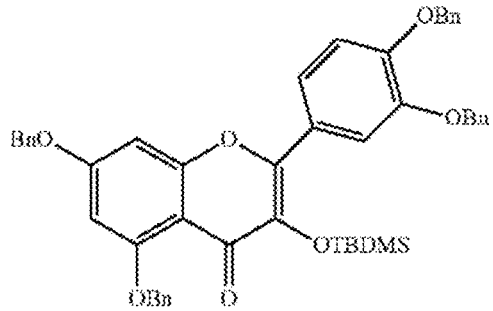

With:
--iii. reducing the compound of formula [4] with LiAlH$_4$ in the presence of a solvent to obtain a mixture comprising a compound of formula [5] and a compound of formula [6];

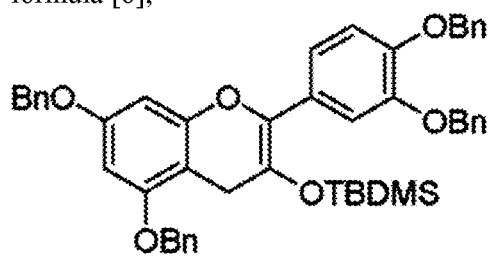
--

At Column 43, Line 2, please replace:
"in the presence of a chiral/achiral reducing agent"
With:
--in the presence of a chiral/achiral reducing agent; and--

At Column 44, Lines 12-19, please replace:

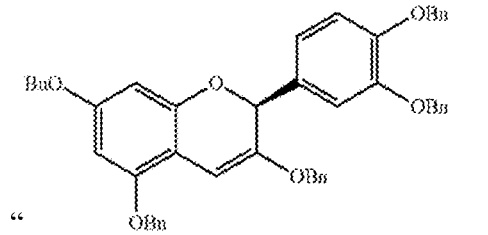

CERTIFICATE OF CORRECTION (continued)
U.S. Pat. No. 9,556,140 B2

With:

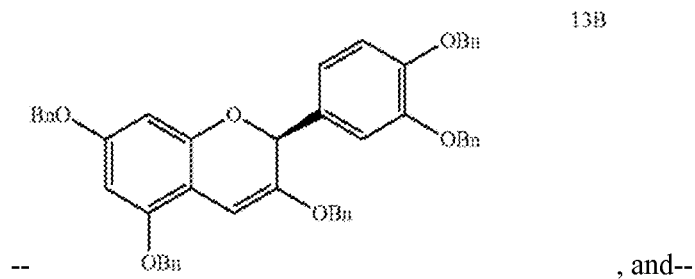

-- , and --